(12) United States Patent
Rooney et al.

(10) Patent No.: US 8,034,223 B2
(45) Date of Patent: *Oct. 11, 2011

(54) METHODS AND APPARATUS FOR LOW RESISTANCE ELECTROPHORESIS OF PRIOR-CAST, HYDRATABLE SEPARATION MEDIA

(75) Inventors: Regina Rooney, La Jolla, CA (US); Bradley Scott, San Diego, CA (US); Joseph Amshey, Encinitas, CA (US); Thomas Jackson, La Jolla, CA (US); Sheldon Engelhorn, Cardiff, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/485,379

(22) Filed: Jun. 16, 2009

(65) Prior Publication Data

US 2009/0314641 A1 Dec. 24, 2009

Related U.S. Application Data

(63) Continuation of application No. 10/464,258, filed on Jun. 17, 2003, now Pat. No. 7,601,251, which is a continuation-in-part of application No. 10/102,188, filed on Mar. 18, 2002, now Pat. No. 6,936,150.

(60) Provisional application No. 60/390,259, filed on Jun. 18, 2002, provisional application No. 60/290,464, filed on May 10, 2001.

(51) Int. Cl.
*G01N 27/447* (2006.01)
*G01N 27/453* (2006.01)

(52) U.S. Cl. ......... 204/466; 204/456; 204/606; 204/616

(58) Field of Classification Search .................. 204/456, 204/466, 467, 606, 616–618
See application file for complete search history.

(56) References Cited

U.S. PATENT DOCUMENTS

| 3,875,044 A | 4/1975 | Renn et al. |
|---|---|---|
| 4,094,759 A | 6/1978 | Ruhenstroth-Bauer et al. |
| 4,130,470 A | 12/1978 | Rosengren et al. |
| 4,374,723 A | 2/1983 | Vesterberg |
| 4,385,974 A | 5/1983 | Shevitz |
| 4,415,428 A | 11/1983 | Nochumson et al. |
| 4,417,967 A | 11/1983 | Ledley |
| 4,443,319 A | 4/1984 | Chait et al. |
| 4,666,581 A | 5/1987 | Itoh et al. |

(Continued)

FOREIGN PATENT DOCUMENTS

DE 19930253 12/2000

(Continued)

OTHER PUBLICATIONS

U.S. Appl. No. 09/633,172, filed Aug. 2000, Champagne, James T.

(Continued)

*Primary Examiner* — Alex Noguerola

(57) ABSTRACT

Methods and apparatus are presented that facilitate electrophoresis of prior-cast, hydratable separation media, usefully immobilized pH gradient (IPG) strips. The method exploits the swelling of prior-cast, hydratable separation media upon rehydration to help lodge the media in an enclosing member that permits spaced electrical communication with the enclosed separation media. The electrical communication permits a voltage gradient to be established in the enclosed separation medium sufficient to effect separation of analytes therein. Cassettes, buffer cores, electrophoresis systems and kits are presented for effecting the methods of the invention.

20 Claims, 19 Drawing Sheets

U.S. PATENT DOCUMENTS

| | | | |
|---|---|---|---|
| 4,693,804 A | 9/1987 | Serwer | |
| 4,746,551 A | 5/1988 | Allen et al. | |
| 5,149,418 A | 9/1992 | Flesher | |
| 5,159,049 A | 10/1992 | Allen | |
| 5,209,831 A | 5/1993 | MacConnell | |
| 5,238,651 A | 8/1993 | Chuba | |
| 5,275,710 A | 1/1994 | Gombocz et al. | |
| 5,389,400 A | 2/1995 | Ting et al. | |
| 5,407,546 A | 4/1995 | Schickle | |
| 5,543,023 A | 8/1996 | Lugojan | |
| 5,593,838 A | 1/1997 | Zanzucchi et al. | |
| 5,699,157 A | 12/1997 | Parce | |
| 5,707,506 A | 1/1998 | Douthart et al. | |
| 5,744,336 A | 4/1998 | Hodges et al. | |
| 5,746,901 A | 5/1998 | Balch et al. | |
| 5,773,645 A | 6/1998 | Hochstrasser | |
| 5,800,690 A | 9/1998 | Chow et al. | |
| 5,827,418 A | 10/1998 | Haven et al. | |
| 5,837,116 A | 11/1998 | Harrington et al. | |
| 5,888,369 A | 3/1999 | Tippins et al. | |
| 5,989,400 A | 11/1999 | Islam | |
| 5,993,627 A | 11/1999 | Anderson et al. | |
| 6,001,233 A | 12/1999 | Levy | |
| 6,013,165 A | 1/2000 | Wiktorowicz et al. | |
| 6,113,766 A | 9/2000 | Steiner et al. | |
| 6,156,182 A | 12/2000 | Olech et al. | |
| 6,398,933 B1 | 6/2002 | Scott | |
| 6,558,522 B1 | 5/2003 | Williams et al. | |
| 6,936,150 B2 | 8/2005 | Rooney et al. | |
| 7,601,251 B2 * | 10/2009 | Rooney et al. | 204/548 |
| 2003/0015426 A1 | 1/2003 | Rooney et al. | |

FOREIGN PATENT DOCUMENTS

| | | |
|---|---|---|
| EP | 1385603 | 2/2004 |
| JP | 62-167460 | 7/1987 |
| JP | 4236938 | 8/1992 |
| WO | WO-94/10561 | 5/1994 |
| WO | WO-98/45693 | 10/1998 |
| WO | WO-98/57161 | 12/1998 |
| WO | WO-98/57162 | 12/1998 |
| WO | WO-99/33550 | 7/1999 |
| WO | WO-00/31526 | 6/2000 |
| WO | WO-01/20315 | 3/2001 |
| WO | WO-02/26773 | 4/2002 |
| WO | WO-02/92200 | 11/2002 |

OTHER PUBLICATIONS

U.S. Appl. No. 09/633,172; Notice of Allowance mailed Nov. 28, 2008.

U.S. Appl. No. 10/102,188; Notice of Allowance mailed Mar. 24, 2005.

U.S. Appl. No. 10/102,188; Office Action mailed Sep. 27, 2004.

U.S. Appl. No. 10/102,188; Office Action mailed Dec. 22, 2003.

U.S. Appl. No. 10/102,188; Response to Sep. 27, 2004 Office Action mailed Jan. 27, 2005.

U.S. Appl. No. 10/102,188; Response to Dec. 22, 2003 Office Action mailed May 24, 2004.

U.S. Appl. No. 10/464,258; Notice of Allowance mailed Apr. 14, 2009.

U.S. Appl. No. 10/464,258; Office Action mailed Sep. 18, 2007.

U.S. 10/464,258; Non-Final Office Action mailed Jan. 25, 2007.

U.S. Appl. No. 10/464,258; Response to Final Office Action mailed Sep. 18, 2008.

U.S. Appl. No. 10/464,258; Response to Non-Final Office Action mailed Jun. 25, 2007.

EP02713876; Supplementary EPO Search Report mailed Nov. 26, 2004.

EP02713876; European Search report mailed Sep. 10, 2004.

PCT/US02/08438; PCT International Search Report mailed Sep. 5, 2002.

WO 2003/106973; PCT Search Report mailed Dec. 29, 2003.

Amersham Pharmacia Biotech, "-2-D Electrophoresis Using Immobilized pH Gradients: Principles and Methods", *Rev. A*, part 80-6429-60, (Sep. 1998); pp. 1-51.

Amersham Pharmacia Biotech, "Immobiline Dry Strip", 1998; pp. 1-4.

Amersham Pharmacia Biotech, "IPGphor IEF System", www.apbiotech.com/stiboasp/showmodule.asp? (Feb. 23, 2001); pp. 1-7.

Bio-Rad Laboratories, "2-D Electrophoresis: ReadyStrip IPG Strips: Part of the ProteomeWorks System", http://www.expressionproteomics.com/LifeScience/pdf/Bulletin_2442.pdf Bulletin 2442 Rev F; pp. 1-2.

Bio-Rad Laboratories, "A Flexible, High Throughput Method for 2-D Protein Separations", EG Bulletin 2217; pp. 1-2.

Bio-Rad Laboratories, "Isoelectric Focusing Cell : Model 111 Mini IEF Cell", *Bio-Rad Laboratories (Life Science Research catalog)* Website Apr. 6, 1997., www.biorad.com/56537.html Apr. 6, 2007; 2 pages.

Bio-Rad Laboratories, "Protean II xi Cell and Protean II xi 2-D Cell Instruction Manual"; pp. 1-49.

Bio-Rad Laboratories, "Protean II xi and XL Multi-Cells:Ordering Information", www.bio-rad.com/B2B/BioRad/Product/br_category.jsp?BV. Original url no longer available. Attachment uploaded Aug. 11, 2008 Feb. 27, 2002, 1-2.

Bio-Rad Laboratories, "Protean II xi Cell IPG Conversion Kit Setup Guide", Feb. 23, 2001; pp. 1-2.

Bio-Rad Laboratories, "Protean II xi multi-cell Instruction Manual Catalog No. 165-1951"; pp. 1-23.

Bio-Rad Laboratories, "Protean II XL Cell for IPG Strips", www.bio-rad.com/B2B/BioRad/product/br_category.jsp?BV Feb. 23, 2002; 1 page.

Bio-Rad Laboratories, "Protein Electrophoresis: Large Precast Gels for 1-D, Protean II Ready Gel Precast Gels for Single-Dimension Gel Electrophoresis".

Bio-Rad Laboratories, "Protein Electrophoresis: Large Precast Gels for 2-D: Part of the ProteomeWorks System, Ready Gel Precast Gels for Two-Dimensional Gel Electrophoresis".

Bio-Rad Laboratories, "ReadyStrip.TM. IPG Strips Instruction Manual", Catalog No. 163-2099; pp. 1-11.

Bio-Rad Laboratories, "The ProteomeWorks System: Now Get More From 2-D".

Bjellqvist, Bengt, "Isoelectric focusing in immobilized pH gradients: principle, methodology and some applications", *Journal of Biochemical and Biophysical Methods*, vol. 6, No. 4, Elsevier Biomedical Press 1982; pp. 317-339.

Bonnet, "Epoxy-Diamine Thermoset/Thermoplastic Blends.1. Rates of Reaction before and after Phase Separation", *Macromolecules*, vol. 32, No. 25, 1999; pp. 8517-8523.

Bonnet, "Epoxy-Diamine Thermoset/Thermoplastic Blends.2. Rheological Behavior before and after Phase Separation", *Macromolecules*, vol. 32, No. 25, 1999; pp. 8524-8530.

Bonnet, "Epoxy-Diamine Thermoset/Thermoplastic Blends: Dielectric Properties before, during, and after Phase Separation", *Macromolecules*, vol. 33, No. 10, 2000; pp. 3833-3843.

Frey, Manuela D., "Preparation of Rehydratable Polyacrylamide gels and Their Application in Ultrathin-Layer Isoelectric Focusing", *Electrophoresis*, vol. 7, 1986; pp. 28-40.

Gorg, Angelika, "The Current State of Two-Dimensional Electrophoresis with Immobilized pH Gradients", *Electrophoresis*, vol. 21, No. 6, 2000; pp. 1037-1053.

Gorg, Angelika, "The Current State of Two-Dimensional Electrophoresis with Immobilized pH Gradients", *Electrophoresis*, vol. 9, No. 9, 1988; pp. 531-546.

Haglund, Herman, "Isoelectric Focusing in pH Gradients-A Technique for Fractionalization and Characterization of Ampholytes", *Methods of Biochemical Analysis*, vol. 19, Interscience Publishers, Edited by David Glick 1971; pp. 1-104.

Hanash, Samir M., "Two-dimensional electrophoresis with immobilized pH gradients in the first dimension: Protein focusing as a function of time", *Electrophoresis*, vol. 8, 1987; pp. 229-234.

Harrington, M.G., "Analytical and Micropreparative Two-Dimensional Electrophoresis of Proteins", *Methods: a Companion to Methods in Enzymology*, vol. 3, No. 2, Oct. 1991; pp. 98-108.

Holter, Dirk, "Liquid Crystalline Thermosets Based on Branched Bismethacrylates", *Macromolecules*, vol. 29, No. 22, 1996; pp. 7003-7011.

Invitrogen Life Technologies, "Ordering Information: ZOOM IPGRunner", http://www.invitrogen.com/content/cfm?pfile=Zoomordering.htm&cfid=4090580&cftoken . . . , Jun. 4, 2002; pp. 1-6.

Invitrogen Life Technologies, "Xcell SureLock Mini-Cell: The Most Convenient, Versatile, Mini-Vertical Electrophoresis System", www.invitrogen.com/content.cfm? pageid=3476&cfid=1359647 &cftoken=23915763, Apr. 18, 2001; pp. 1-5.

Invitrogen Life Technologies, "ZOOM into Fast and Accurate Results: The ZOOM® IPGRunner System", 2002.

Invitrogen Life Technologies, "ZOOM IPGRunner", http://www.invitrogen.com/content.cfm?pageid=4206&cfid=4090580 &cftoken=71290592 site since redesigned, original url not available. Attachment is based on search: Zoom IPGRunner done on Aug. 11, 2008, Jun. 4, 2002; pp. 1-9.

Invitrogen Life Technologies, "ZOOM IPGRunner System for Isoelectric Focusing of ZOOM Strips", *Catalog Nos. ZM0001, ZM0002, ZM0004 Version A, Instruction Manual*, 2002.

Invitrogen Life Technologies, "Zoom System", Original: http://www.invitrogen.com/images/ZOOM_ System.jpg Attachment found: http://web.archive.org/web/20020921083853/http://invitrogen.com/images/ZOOM_System.jpg, Jun. 4, 2002; 1 page.

Islam, Reza, "A New Approach to Rapid Immobilized pH Gradient IEF for 2-D Electrophoresis", *Science Tools from Amersham Pharmacia Biotech*, vol. 3, No. 1, 1998; pp. 14-15.

Righetti, Pier G., "Immobilized pH Gradient: Theory and Methodology", *Laboratory Techniques in Biochemistry and Molecular Biology*, vol. 20, Chapters 2 and 3, 1990.

Righetti, Pier G., "Immobilized pH Gradients", *Trends in Biochemical Sciences*, vol. 13, No. 9, Sep. 13, 1988; pp. 335-338.

Righetti, Pier G., "Isoelectric Focusing in Gels", *Journal of Chromatography*, vol. 98, No. 2, Sep. 25, 1974; pp. 271-321.

Righetti, Pier G., "Isoelectric Focusing in Immobilized pH Gradients", *Methods in Enzymology*, vol. 270, 1996; pp. 235-255.

Righetti, Pier G., "Isoelectric Focusing in Immobilized pH Gradients: An Update", *Journal of Chromatography B*, vol. 699, No. 1-2, Oct. 10, 1997; pp. 77-89.

Yoon, Pil J., "Effect of Thermal History of the Rheological Behavior of Thermoplastic Polyurethanes", *Macromolecules*, vol. 33, No. 6, Mar. 3, 2000; pp. 2171-2183.

* cited by examiner

_US 8,034,223 B2_

METHODS AND APPARATUS FOR LOW RESISTANCE ELECTROPHORESIS OF PRIOR-CAST, HYDRATABLE SEPARATION MEDIA

CROSS-REFERENCE TO RELATED APPLICATIONS

This application is a continuation and claims the right of priority under 35 U.S.C. §120 to U.S. application Ser. No. 10/464,258, filed Jun. 17, 2003, now U.S. Pat. No. 7,601,251; which claims the benefit of U.S. provisional application Ser. No. 60/390,259, filed Jun. 18, 2002, and which is a continuation-in-part of U.S. application Ser. No. 10/102,188, filed Mar. 18, 2002, now U.S. Pat. No. 6,936,150; which claims the benefit of U.S. provisional application Ser. No. 60/290,464, filed May 10, 2001, all of which are commonly assigned with the instant application, and the disclosures of all of which are hereby expressly incorporated by reference in their entirety as though fully set forth herein.

FIELD OF THE INVENTION

The present invention relates to methods and apparatus for electrophoresis of prior-cast hydratable separation media. In particular, the invention relates to methods, cassettes, buffer cores, and systems useful for conducting isoelectric focusing using immobilized pH gradient (IPG) strips.

BACKGROUND OF THE INVENTION

For over thirty years, isoelectric focusing (IEF) has served as a primary tool for analyzing proteins present in complex admixture, such as proteins present in biological samples.

In isoelectric focusing, proteins are driven by an applied electric field through a pH gradient typically established in a support matrix, such as a gel. Proteins migrate until the isoelectric point (pI) of the protein coincides with the local pH; at that point, the protein no longer bears net charge and ceases to migrate, becoming focused at a point that is characteristic of the protein.

As originally described, the pH gradient for IEF was established and sustained in the gel matrix by mobile carrier ampholytes (CA). Gels typically would be polymerized in the presence of a population of CA having a range of charge characteristics; upon application of a voltage gradient, the various species of CA would align themselves in the matrix to establish a pH gradient across the gel.

Although IEF with CA has proven tremendously useful, it was soon discovered that pH gradients created by CA were susceptible to titration by atmospheric carbon dioxide, leading to the migration of CA towards the cathode and destruction of the pH gradient over time, a phenomenon termed cathodic drift.

Cathodic drift can be reduced by casting IEF gels in enclosed tubes, thus limiting exposure to atmospheric $CO_2$. However, the tube traps prepolymer component impurities in the matrix during polymerization, interfering with separation. Furthermore, the tube format presents difficulties when a second dimension of separation, such as fractionation by size, is desired.

In a different approach to the problem of cathodic drift, Bjellqvist and colleagues immobilized the pH gradient in the support matrix, an approach now termed immobilized pH gradient (IPG) isoelectric focusing. See Bjellqvist et al., _J. Biochem. Biophys. Methods_ 6(4):317-39 (1982); Righetti et al., _Trends Biochem. Sci._ 13(9):335-8 (1988); Righetti et al., _Methods Enzymol._ 270:235-55 (1996); U.S. Pat. No. 4,130,470; and Righetti, _Immobilized pH Gradient: Theory and Methodology_, (Laboratory Techniques in Biochemistry and Molecular Biology, Vol. 20), Elsevier Biomedical Press, LTD, Netherlands (ASIN: 0444813012). Two-dimensional electrophoresis, with IPG IEF followed by size fractionation, soon followed. Gorg et al., _Electrophoresis_ 9(9):531-46 (1988).

IPG not only reduced the problem of cathodic drift, but also proved useful in reducing interference from prepolymer component impurities, since the IPG strip's plastic backing imparts sufficient structural resilience to the gel as to permit the gel to be washed before use. The increased resilience also permits the gels to be stored in dehydrated form before use. Dehydrated IPG strips are today sold in a variety of pH ranges and a variety of separation lengths by a number of vendors (e.g., Immobiline DryStrip Gels, Amersham Biosciences, Piscataway, N.J., USA; ReadyStrip IPG, Bio-Rad Laboratories, Hercules, Calif., USA).

Problems Remain, However.

Although immobilization of the gradient-forming ampholytes prevents cathodic drift, the charge-bearing immobilized moieties (immobilines) remain susceptible to titration by atmospheric $CO_2$. $CO_2$ titration is exacerbated by the fact that the separation medium of IPG strips is directly exposed to air on at least one side. Direct exposure to air also leads to possible dehydration of the matrix, with possible salt crystallization, during electrophoresis.

These problems have been addressed in part by a methodological, rather than structural, solution: plastic-backed IPG strips are typically electrophoresed under an occlusive oil layer, which both excludes air and retards evaporation.

Use of an occlusive liquid oil layer presents its own difficulties, however. Principal among these is the requirement that electrophoresis be performed with the IPG strip maintained in a horizontal orientation. The obligate horizontal orientation precludes use of the smaller-footprint, vertical electrophoresis devices typically used for SDS-polyacrylamide gel electrophoresis (SDS-PAGE), such as those described in Tippins et al., U.S. Pat. No. 5,888,369. In addition, the use of oil requires deft manual technique and proves time-intensive.

Wiktorowicz et al., U.S. Pat. No. 6,013,165, describe an apparatus in which immobilized pH gradient isoelectric focusing can be performed without use of a liquid oil layer. A continuous pKa gradient is immobilized on at least one of the major opposing surfaces of a cavity formed between two plates. The cavity, which can be further segmented into parallel channels, is then filled with a flowable separation medium. Electrophoresis is preferably conducted with the assembly oriented horizontally to minimize convection currents in the flowable separation medium. The apparatus does not readily permit insertion of prior-cast hydratable separation media, such as commercial IPG strips, nor does it readily permit electrophoresis in the vertical dimension.

There thus exists a need in the art for methods and apparatus that allow IPG strips, and other prior-cast hydratable separation media, to be electrophoresed without requiring contact with an occlusive fluid oil layer. There further exists a need in the art for methods and apparatus that allow IPG strips, and other prior-cast hydratable separation media, to be electrophoresed in a vertical orientation.

SUMMARY OF THE INVENTION

The present invention solves these and other needs in the art by providing methods, apparatus, and kits for electrophoresis of prior-cast hydratable separation media that obviate the use of an occlusive oil layer, thereby obviating the requirement that electrophoresis be performed in the horizontal orientation.

The present invention is based, in part, upon the discovery that the swelling that attends rehydration of prior-cast hydratable separation media can be exploited to help lodge such media in an enclosure that permits spaced electrical communication with the enclosed separation medium. The spaced electrical communication makes it possible to apply a voltage gradient to the prior-cast hydratable separation media while the medium is otherwise enclosed, permitting electrophoresis to be conducted within a cassette.

Enclosed, the separation medium's contact with air is substantially reduced. In cases in which the prior-cast hydratable separation medium is an IPG strip, the reduction in air contact obviates the prior art requirement for occlusive contact with a fluid oil layer during immobilized pH gradient isoelectric focusing.

Enclosed, and lacking an attendant fluid oil layer, the prior-cast separation medium can be electrophoresed in any physical orientation. In cases in which the prior-cast hydratable separation medium is an IPG strip, relaxation of the prior-art requirement for horizontal electrophoresis makes it newly possible to perform IPG electrophoresis using the widely distributed, small footprint, vertical electrophoresis gel boxes presently used to perform SDS-PAGE.

The invention is further based upon novel apparatus designs that minimize the resistance between power supply and gel; the reduction in parasitic system impedances permits separations, particularly isoelectric focusing in IPG strips, to be performed using lower voltages for reduced times.

Thus, in a first aspect, the invention provides a method for performing electrophoresis, comprising: hydratingly lodging a prior-cast hydratable electrophoretic separation medium within an enclosing member that permits spaced electrical communication with the enclosed medium; and then using the spaced electrical communication to establish a voltage gradient in the enclosed separation medium sufficient to effect electrophoretic separation of analytes therein.

In one embodiment, the method further comprises the antecedent step of inserting the prior-cast hydratable electrophoretic separation medium in its dehydrated state into the enclosing member. In another embodiment, the method further includes a later step of removing the prior-cast hydratable electrophoretic separation medium from the enclosing member. The medium once removed can be used, for example, to apply the one-dimensionally fractionated sample to a gel to effect a second dimension of separation.

In some embodiments, the step of hydratingly lodging comprises: contacting the dehydrated prior-cast hydratable electrophoretic separation medium with an aqueous solution, often an aqueous solution that includes the sample to be fractionated.

The methods of the present invention are particularly useful in performing isoelectric focusing using immobilized pH gradient strips. Thus, the prior-cast hydratable electrophoretic separation medium used in the practice of the present invention can usefully have an immobilized pH gradient.

As described above, the methods of the present invention include the use of an enclosing member that has (i) means for hydratingly lodging a prior-cast electrophoretic separation medium therewithin, and (ii) means for spaced electrical communication with the enclosed separation medium, wherein the spaced electrical communication means can be used to apply a voltage gradient to the enclosed medium sufficient to effect electrophoretic separation of analytes present therewithin.

Thus, in another aspect, the invention provides a cassette for performing electrophoresis, comprising: means for hydratingly lodging a prior-cast electrophoretic separation medium within an enclosing member; and means for spaced electrical communication with the enclosed medium, wherein the spaced electrical communication means can be used to establish a voltage gradient in the separation medium sufficient to effect electrophoretic separation of analytes therein.

In certain embodiments, the cassette of the present invention comprises: a form-retaining member, and at least one channel, wherein the form-retaining member imparts dimensional integrity to the channel or channel(s). In typical embodiments, the cassette includes a plurality of such channels.

Each channel present in the cassette and useful for performing the methods of the present invention has a first channel entry, a second channel entry, and a cavity therebetween, the channel cavity being so dimensioned as to permit insertion of a hydratable prior-cast electrophoretic separation medium in its dehydrated state and lodgingly enclose the strip in its rehydrated state. The first and second channel entries permit spaced electrical communication with the channel cavity; the spaced electrical communication permits current to be flowed through the channel cavity.

In some embodiments, the form-retaining member contributes the entire circumferential wall of the cavities of the channels. In other, multilaminate embodiments, the cassette further comprises a laminate cover; the laminate cover adheres directly or indirectly to the form-retaining member and contributes at least part of the circumferential wall of said channels. In these latter embodiments, the adherence of the laminate cover to the form-retaining member is typically reversible.

In other embodiments, the cassette further comprises a first well-forming member, which adheres directly or indirectly to the form-retaining member, and which defines fluid reservoirs at a plurality of first channel entries. Usefully, the cassette can further comprise a second well-forming member, the second well-forming member adhering, directly or indirectly, to the form-retaining member and defining fluid reservoirs at a plurality of second channel entries. When present, the well-forming members can usefully be reversibly adherent to the form-retaining member.

In one series of related embodiments, the first and second channel entries for each of the channels permit electrical communication with the intervening channel cavity through a common surface of the cassette. In another series of related embodiments, the first and second channel entries permit electrical communication with their intervening cavity through separate surfaces of the cassette. These two mutually exclusive geometries call for different electrode geometries, and thus different electrophoresis buffer cores, to complete the circuits required for electrophoresis.

The prior-cast hydratable electrophoretic separation medium can be provided by the user, can be included within one or more channels of the cassette without requirement for user insertion thereof, or can be provided separately packaged with the cassette in a kit.

As to the latter, it is another aspect of the present invention to provide kits for facilitating electrophoresis of prior-cast hydratable electrophoretic separation media. The kits typically comprise a cassette of the present invention and at least one prior-cast hydratable electrophoretic separation medium suitably dimensioned as to be hydratingly lodgeable in said cassette.

In some embodiments, the kit includes a cassette and at least one conductive wick for use therewith; often, in such kits, a sufficient number of wicks are provided to facilitate both anodic and cathodic connections with the cassette.

The cassettes of the present invention can be used to effect vertical electrophoresis of prior-cast hydratable separation media, usefully in the buffer tanks that are commonly used, with buffer cores, for SDS-PAGE electrophoresis. In cassette embodiments in which the first and second channel entries open to separate surfaces of the cassette, buffer cores presently used for SDS-PAGE electrophoresis can be used. In cassette embodiments in which the first and second channel entries open to the same surface of the cassette, alternative buffer core geometries are required.

Thus, it is another aspect of the present invention to provide a buffer core for vertical electrophoresis of pre-cast hydratable electrophoretic separation media, comprising: a substantially inflexible frame, an anode, and a cathode in spaced relationship to the anode. The buffer core frame has a first cassette engagement face and a second cassette engagement face. Operational engagement of a first and second cassette to the respective first and second frame engagement faces creates a chamber internal to the frame that is sealed on 5 sides. The cathode and anode are each in electrical communication with the interior of the internal chamber, and operational engagement of a first and second cassette to the respective first and second frame engagement faces causes spaced contact of the anode and cathode to the surface of at least one cassette that engages the frame engagement surface, allowing electrophoresis of prior-cast hydratable separation media enclosed therein.

The cassette and buffer core system of the present invention reduces the resistance between power supply and gel, permitting electrophoretic separation using lower voltages, for shorter times, for a lower volt-hour total.

Thus, in another aspect, the invention provides a system for low resistance electrophoresis of analyte samples in prior-cast, hydratable separation media strips. The system comprises means for enclosing a plurality of strips and means responsive to an external compressive force for effecting spaced electrical communication by a single anode and single cathode simultaneously with each of said enclosed strips.

The enclosing means permits spaced electrical communication separately with each of the enclosed strips through respective first and second entries. The electrical communication means is capable of distributing an external compressive force to urge the anode and the cathode toward the enclosing means with greater pressure at the first and second entries than elsewhere on the enclosing means.

The electrical communication means may comprise an anode support; a cathode support; an anode; and a cathode. The supports in these embodiments discontinuously distribute an external compressive force to the anode and cathode to urge the anode and cathode toward the enclosing means with greater pressure at the first and second entries than elsewhere on the enclosing means. In certain embodiments, the anode support makes discontinuous contact with the anode and the cathode support makes discontinuous contact with the cathode.

In typical embodiments of the system of this aspect of the invention, the enclosing means is capable of hydratingly lodging strips there within.

The system provides a substantially reduced resistance pathway between power supply and gel than do prior art devices for electrophoresis of prior-cast, hydratable, separation media, such as IPG strips.

The system of this aspect of the invention may, for example, be capable of effecting electrophoretic separation, including isoelectric focusing in IPG strips, with application of a maximum of 3000 or fewer volts, 1500 or fewer volts, even 500 or fewer volts. The system may be capable of effecting electrophoretic separation, including isoelectric focusing in IPG strips, with application of fewer than 2000 volt-hours, even as few as 1500 volt-hours. The system of this aspect of the invention may be capable of effecting electrophoretic separation, including isoelectric focusing in IPG strips, in fewer than 6 hours, 5 hours, even 4 hours or less.

In another aspect, the invention provides a method for low resistance electrophoresis of analyte samples in prior-cast, hydratable separation media strips.

The method comprises hydratingly lodging at least one strip within an enclosing member that permits separate, spaced, electrical communication with each of a plurality of enclosed strips through respective first and second entries; applying a sample containing protein analytes to the enclosed strip; forcibly urging an anode and a cathode toward the enclosing member to effect simultaneous spaced electrical communication with each of the enclosed strips, wherein the force urging the anode and the cathode toward the enclosing member is distributed to create greater contact pressure at the first and second entries than elsewhere on the enclosing member; and then applying electrical potentials to the anode and cathode at a potential difference and for a time sufficient to effect electrophoretic separation of analytes in the enclosed strips.

In some embodiments, sample is applied during lodging of the strip in said enclosing member.

The method provides a substantially lower resistance pathway between power supply and separation media than is found in the prior art.

Accordingly, effective separation, including isoelectric focusing in IPG strips, may be obtained in the methods of this aspect with application of a maximum of 3000 or fewer volts, 1500 or fewer volts, even 500 or fewer volts. The methods may effect electrophoretic separation, including isoelectric focusing in IPG strips, with application of fewer than 2000 volt-hours, even as few as 1500 volt-hours. The methods may be capable of effecting electrophoretic separation, including isoelectric focusing in IPG strips, in fewer than 6 hours, 5 hours, even 4 hours or less.

In the methods of this aspect of the invention, the potential difference may be applied in a plurality of ramped voltage steps, in a plurality of stepped voltage steps, or at a constant voltage level.

The strip may usefully be an IPG strip.

In a related aspect, the invention provides improved methods of electrophoresis using prior-cast, hydratable, separation media strips, wherein the improvement comprises spacedly contacting the strips with an anode and cathode with resistance between power supply and gel sufficiently low as to permit electrophoretic separation with a maximum applied voltage of no more than 3000 volts, no more than 1500 volts, even no more than 500 volts.

In various embodiments of the methods of this aspect of the invention, the strip is an immobilized pH gradient (IPG) strip, and the resistance is sufficiently low as to permit isoelectric focusing with application of fewer than 2000 nominal volt-hours, even as few as 1500 nominal volt-hours.

In yet another aspect, the invention provides a buffer core device for forcibly urging an anode and a cathode into simultaneous spaced electrical communication with a plurality of prior-cast hydratable separation media strips enclosed within means that permit spaced electrical communication separately with each of the enclosed strips through respective first and second entries.

The device comprises a substantially inflexible frame; an anode support; a cathode support; an anode; and a cathode. The anode support and the cathode support are spacedly fixed to the frame and are capable of distributing an external compressive force respectively to the cathode and the anode to urge the cathode and the anode toward the enclosed strips with greater contact pressure at the first and second entries than elsewhere on the enclosing means.

The anode support may make intermittent contact with the anode and the cathode support may make intermittent contact with the cathode.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which.

DETAILED DESCRIPTION

Figure 1A:
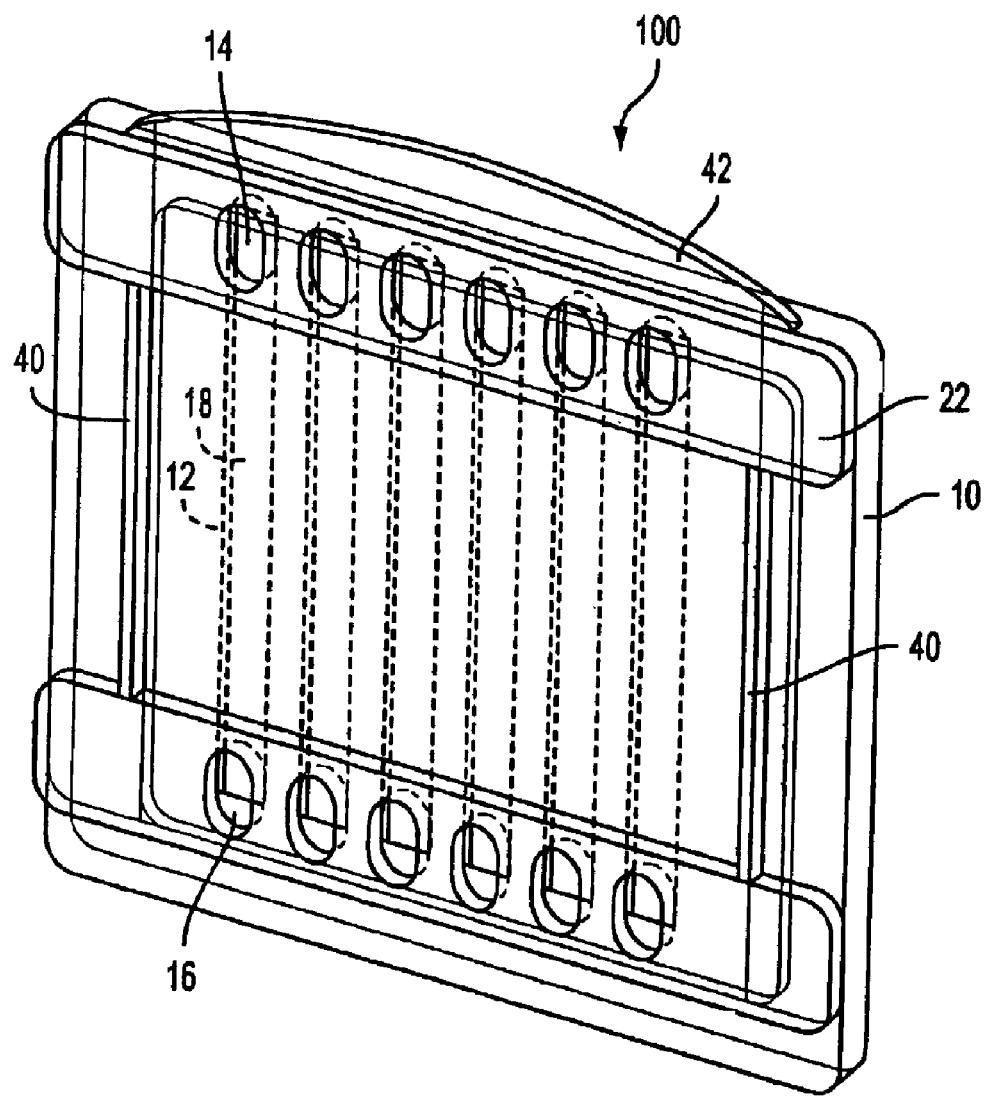
FIG. 1A is a front perspective view of one embodiment of a cassette of the present invention.

The present invention is based, in part, upon the discovery that the swelling that attends rehydration of prior-cast hydratable separation media can be exploited to help lodge such media in an enclosure that permits spaced electrical communication with the enclosed separation medium. The spaced electrical communication makes it possible to apply a voltage gradient to the prior-cast hydratable separation media while the medium is lodged within the enclosing member.

Enclosed, the separation medium's contact with air is substantially reduced. In cases in which the prior-cast hydratable separation medium is an IPG strip, the reduction in air contact obviates the prior art requirement for occlusive contact with a fluid oil layer during immobilized pH gradient isoelectric focusing.

Enclosed, and lacking an attendant fluid oil layer, the prior-cast separation medium can be electrophoresed in any physical orientation. In cases in which the prior-cast hydratable separation medium is an IPG strip, relaxation of the prior-art requirement for horizontal electrophoresis makes it newly possible to perform IPG electrophoresis using the widely distributed, small footprint, vertical electrophoresis gel boxes presently used to perform SDS-PAGE.

In a first aspect, therefore, the invention provides a method for performing electrophoresis, particularly for performing electrophoresis using prior-cast, hydratable separation media. As used herein, the term "electrophoresis" explicitly includes isoelectric focusing.

In a first step, the method comprises hydratingly lodging a prior-cast hydratable electrophoretic separation medium within an enclosing member that permits spaced electrical communication with the enclosed media. In a second step, the spaced electrical communication is used to apply a voltage gradient to the enclosed medium sufficient to effect electrophoretic separation of analytes therein.

As used herein, the phrase "prior-cast electrophoretic separation medium" (and equivalently, "prior-cast separation medium") refers to an electrophoretic separation medium, typically a polymeric gel, that has first been solidified, or gelled, elsewhere than in the enclosing member in which electrophoresis is to be performed.

Electrophoretic separation media, and methods of preparing, casting, and performing electrophoresis using electrophoretic media, are well known in the analytical arts, and need not be detailed here. See, e.g., Rabilloud (ed.), *Proteome Research: Two-Dimensional Gel Electrophoresis and Identification Methods*, Springer Verlag, 2000 (ISBN: 3540657924); Westermeier, dimension substantially greater than a second dimension—such dimensions are not required for practice of the present invention. Nonetheless, for ease of description, all prior-cast electrophoretic separation media useful in the practice of the present invention are referred to in the alternative herein as "strips".

A "prior-cast hydratable electrophoretic separation medium" is a prior-cast electrophoretic medium that can be dehydrated and that, after rehydration, has retained sufficient structural integrity to permit electrophoretic separation of analytes there within.

Neither complete removal of moisture, during dehydration, nor complete saturation with liquid, during rehydration, is required or intended. It suffices for practice of the present invention that the prior-cast, hydratable, electrophoretic separation medium swell detectably after contact in its dehydrated state with an aqueous solution ("aqueous buffer", "buffer").

Typically, the prior-cast hydratable electrophoretic separation medium will swell at least about 5% in volume, often at least about 10%, 15%, 20%, even at least about 25%, 30%, 40% or more in volume upon contact with an aqueous buffer. The volume increase can be manifest in all three dimensions or, when the separation medium is backed with an inextensible layer, principally in one or in two dimensions. The volume increase can occur over a period of minutes or, in the case of IPG strips, more typically over a period of hours.

The degree of swelling is sufficient if the prior-cast, hydratable, electrophoretic separation medium swells sufficiently upon contact with an aqueous solution *Electrophoresis in Practice*, 2nd ed., John Wiley & Sons, 2000 (ISBN 3527300708); B. D. Hames et al. (eds.), *Gel Electrophoresis of Proteins*, 3rd ed., Oxford University Press, 1998 (ISBN 0199636419); and Jones, *Gel Electrophoresis: Nucleic Acids: Essential Techniques*, (John Wiley & Son Ltd. 1996) (ISBN 0471960438), the disclosures of which are incorporated herein by reference in their entireties.

Although polyacrylamide (that is, a polymerization product of acrylamide monomer crosslinked with N,N'-methylenebisacrylamide) and agarose are the two polymeric gels most commonly used in electrophoresis today, the present invention proves useful in electrophoresing a far wider variety of polymeric gels.

Because the gel is first solidified, or gelled, elsewhere than in the enclosing member in which electrophoresis is to be performed, the "prior-cast electrophoretic separation medium" used in the present invention must have sufficient structural resiliency to be transferred or released from its casting mold and thereafter lodged within the enclosure of the present invention.

Typically, such structural resiliency will be imparted to the separation medium by the adherence thereto or incorporation therein of a layer or lamina of another material, such as plastic. Such layers are known in the art, and include, e.g., polyester film backings, as are found in commercial IPG strips, and polyester mesh fabric, which can be incorporated into the separation medium.

Although the "prior-cast electrophoretic separation medium" used in the present invention is typically fashioned as a strip—that is, with a first ("aqueous buffer", "buffer") as to permit hydratable lodging in an enclosing member.

By "hydratable lodging" is intended that the prior-cast, hydratable separation medium be insertable into an enclosing member in its dehydrated state, and that it become lodged in the enclosing member in its rehydrated state.

Although the strip must be "insertable" in its dehydrated state, the strip need not necessarily be removable from the enclosing member in its dehydrated state.

The rehydrated prior-cast hydratable separation medium is said to be "lodged" in the enclosing member (equivalently, "lodgingly enclosed" therein) when two conditions are met. First, the strip remains within the enclosing member when the enclosing member is brought into vertical orientation. Second, when the enclosing member is brought into vertical orientation, at least 50% of the separation medium is precluded from direct communication with ambient atmosphere. Furthermore, although frictional and surface tension forces between the rehydrated separation medium and the enclosing member can contribute to the strip's lodging therein, it is not intended that such frictional or surface tension forces be sufficient in themselves to effect lodging of the strip within the enclosing member.

The enclosing member will be sufficiently form-retaining as to be able to maintain dimensional integrity when maintained in contact with a prior-cast, hydratable separation medium that is swelling. In certain embodiments described in detail below, the enclosing member is a cassette having a form-retaining channel cavity within which the prior-cast, hydratable separation medium is engaged.

The enclosing member further permits spaced electrical communication with the enclosed prior-cast hydratable separation medium. Communication can be direct, as by throughpassage of anode and cathode electrodes, or indirect, as by passage of current through an intermediate polymer layer or wick, as will be further discussed below.

After the prior-cast hydratable electrophoretic separation medium is lodged in the enclosing member, the spaced electrical communication is used to apply a voltage gradient sufficient to effect electrophoretic separation of analytes therein.

Although described particularly herein as application of a voltage gradient to the separation medium, it is understood that current is thereby caused to flow through the separation medium, and that the method could equally be described as flowing current through the separation medium.

The electrical parameters to be used depend upon the composition and dimensions of the enclosed electrophoretic medium, the composition of the sample, the composition of the rehydration solution, the type of desired separation, and the method by which spaced electrical contact is made with the enclosed separation medium, and can readily be determined empirically by routine experimentation. Particular electrical parameters for isoelectric focusing using cassette-immobilized IPG strips and a buffer core adaptor of the present invention are further described herein below.

Returning to the method in more detail, the prior-cast hydratable electrophoretic separation medium is typically inserted by the user in its dehydrated state in the enclosing member.

By way of example, in embodiments further described below, the prior-cast hydratable separation medium, such as an IPG strip, is movably inserted by hand into a channel cavity present within the enclosing member. As another example, where the enclosing member is hinged, or otherwise reversibly separable, the prior-cast hydratable separation medium, such as an IPG strip, is movably inserted by hand into a depression, with the channel cavity thereafter completed by closing the member.

Although typical, movable insertion of the dehydrated strip into the enclosing member is not always required. For example, the dehydrated strip can be earlier-inserted during manufacture of the enclosing member, obviating insertion of the dehydrated prior-cast separation medium into the enclosing member by the user.

The dehydrated separation medium is then contacted with an aqueous solution.

The composition of the rehydration solution will depend upon the composition of the sample and separation medium and the intended electrophoretic procedure, and its choice will thus depend on factors that are well known in the electrophoretic arts.

For example, where the prior-cast hydratable separation medium is a commercial IPG strip, such as an Immobiline DryStrip (Amersham Biosciences, Piscataway, N.J., USA), the rehydration solution can usefully include urea, non-ionic or zwitterionic detergents, dithiothreitol (DTT), dye, and a carrier ampholyte mixture suited to the pH range of the IPG strip. Carrier ampholyte mixtures for use in such rehydration solutions are available commercially (e.g., IPG Buffer pH 3.5-5.0, cat. no. 17-6002-02; IPG Buffer pH 4.5-5.5, cat. no. 17-6002-04; IPG Buffer pH 5.0-6.0, cat. no. 17-6002-05; IPG Buffer pH 5.5-6.7, cat. no. 17-6002-06; IPG Buffer pH 4-7, cat. no. 17-6002-86; IPG Buffer pH 6-11, cat. no. 17-6002-78; IPG Buffer pH 3-10 NL, cat. no. 17-6002-88; IPG Buffer pH 3-10, cat. no. 17-6002-87, all from Amersham Biosciences, Piscataway, N.J., USA).

The rehydration solution can also advantageously include the sample intended to be separated in the prior-cast hydratable separation medium.

For example, in cases in which the prior-cast hydratable electrophoretic separation medium is an IPG strip, the sample to be separated can be a mixture of proteins, such as those from a biological sample, and can usefully be or have been denatured, as by chaotropes, reducing agents, and detergents. In cases in which the separation medium is other than an immobilized pH gradient strip, the sample can include other types of macromolecules, such as nucleic acids.

The methods of the present invention can include the later step of removing the prior-cast hydratable separation medium from the enclosing member after electrophoresis. The method of removal will depend on the structure of the enclosing member, as will be further described below. As an alternative to removal, the separation medium in certain embodiments of the methods of the present invention can be further analyzed within the enclosing member, such as by staining and drying.

As described above, the methods of the present invention include the use of an enclosing member that has (i) means for hydratingly lodging a prior-cast electrophoretic separation medium therewithin and (ii) means for spaced electrical communication with the enclosed separation medium, wherein the spaced electrical communication means can be used to apply a voltage gradient to the enclosed separation medium sufficient to effect electrophoretic separation of analytes present therewithin.

It is, therefore, another aspect of the present invention to provide an enclosing member useful in the practice of the methods of the present invention, which enclosing member is hereinafter called a "cassette".

Figure 1B:
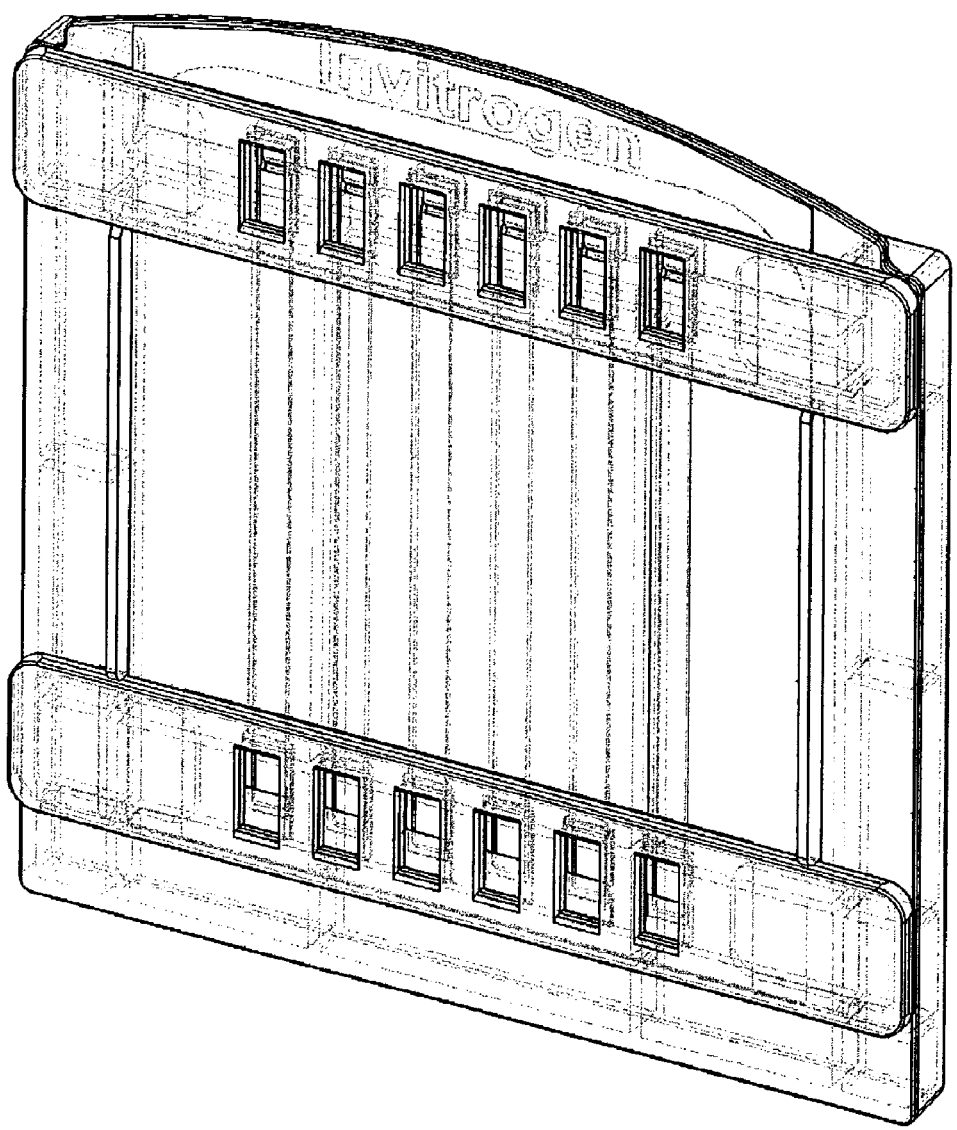
FIG. 1B is a front perspective view of another embodiment of a cassette of the present invention.
Figure 1C:
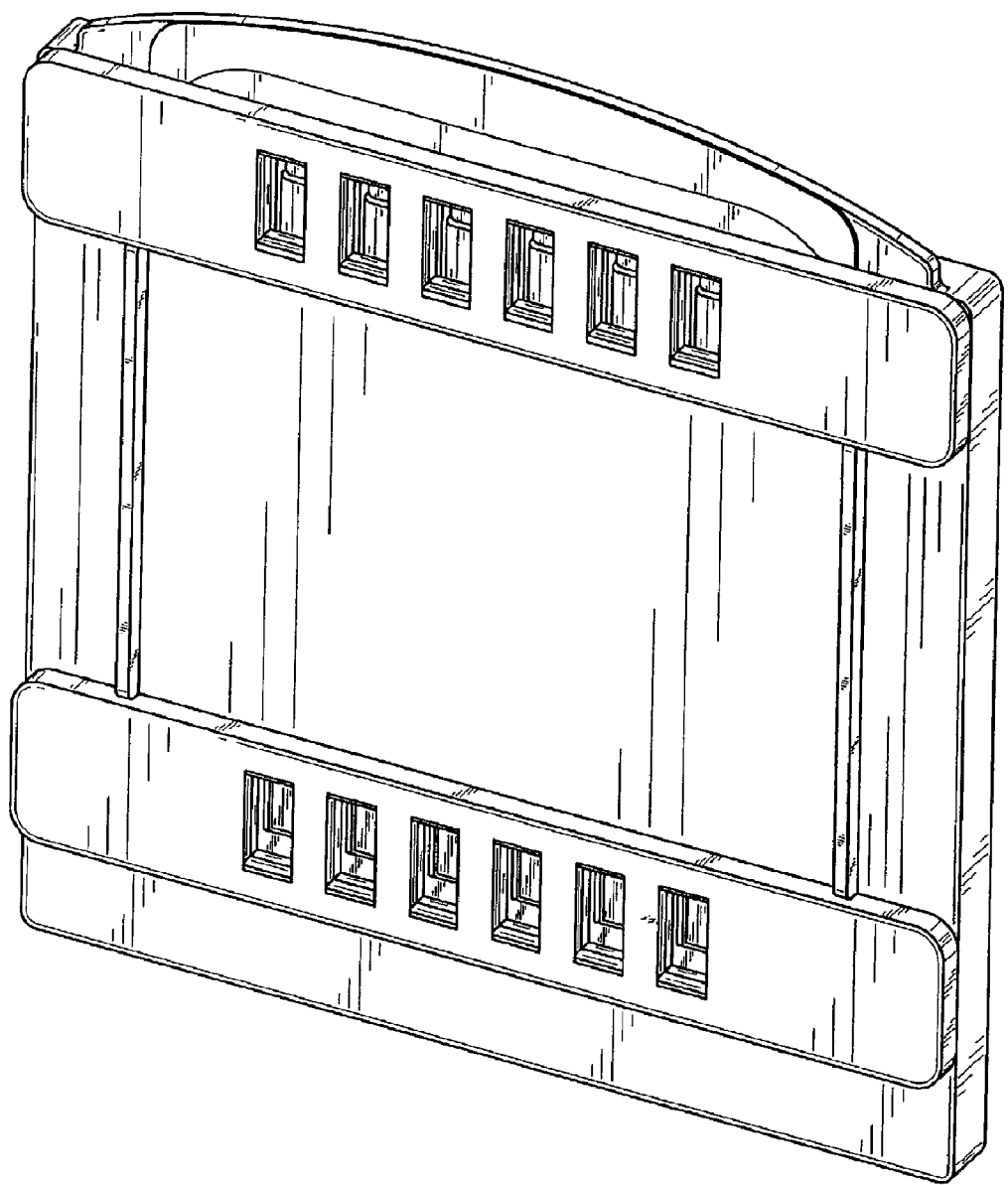
FIG. 1C is a front perspective view of the embodiment of FIG. 1B, rendered as opaque.

FIGS. 1A-1C are front perspective views of embodiments of a cassette of the present invention.

Cassette 100 comprises form-retaining member 10 and at least one channel 12 (in the embodiments shown in FIGS. 1A and 1B, cassette 100 has six substantially parallel channels 12, although fewer or greater numbers can be present). Form-retaining member 10 imparts dimensional integrity to prior-formed channels 12. Channels 12, although present, are not visible in FIG. 1C, rendered as fully opaque.

Referring again to FIG. 1A, channel 12 has first channel entry 14 and second channel entry 16 and cavity 18 therebetween. Cavity 18 of channel 12 is so dimensioned as to movingly engage a prior-cast hydratable electrophoresis medium ("strip"), such as an IPG strip, in its dehydrated state, and to lodgingly enclose the strip after hydration thereof.

First channel entry 14 and second channel entry 16 permit electrical communication with cavity 18, and thus define a channel current flow axis through cavity 18. In certain embodiments of cassette 100 particularly designed for use with buffer cores of the prior art (see below), the channel current flow axis is in a plane substantially parallel to a substantially planar first surface of form-retaining member 10.

To use cassette 100 in the methods of the present invention, rehydratable electrophoresis strip 20, such as an IPG strip, is inserted in its dehydrated state into channel 12, typically through entry 14 or entry 16. In alternative embodiments, strip 20 has been prior-inserted into cassette 100, either by the user or by the manufacturer thereof.

Strip 20 is rehydrated within channel 12 by application of a rehydration solution, optionally containing the sample to be fractionated.

Rehydration solution is typically dispensed into channel 12 prior to insertion of strip 20, since insertion of strip 20 into channel 12 is facilitated by wetting of the interior of channel 12. Strip 20 can, however, be prior-inserted into channel 12, with rehydration solution thereafter applied at either or both of entries 14 and 16. For samples requiring long rehydration times, entry 14, entry 16, or both can be sealed—e.g. with tape or cover slip—to prevent evaporation and the accidental discharge of rehydration solution.

Upon rehydration, strip 20 becomes lodged in cavity 18 of channel 12, at least in part due to swelling of the separation medium. Strip 20 is thereafter not readily removed from channel 12 without expansion of cavity 18, as further described below.

If the sample to be electrophoretically fractionated is not included in the rehydration solution, sample is then applied at entry 14, entry 16, or both with the cassette oriented horizontally to retain sample, and allowed to enter the separation medium. Alternatively, sample can be prior-absorbed into a wick which is then inserted into entry 14, entry 16, or both, from which wick the sample then enters the separation medium. As further described below, sample entry can be facilitated by application of electrical current.

Electrophoresis is then performed by applying a voltage gradient to strip 20, causing current to flow along the channel current flow axis.

Thereafter, strip 20 is typically removed from channel 12 for further processing, such as staining and/or contacting of strip 20 (or a portion thereof) to a gel to effect separation along a second dimension. Removal is typically effected by expansion of cavity 18 using a method appropriate to the composition of cassette 100; for example, in embodiments of cassette 100 in which one or more laminae contribute to the circumferential walls of cavity 18, removal can be effected by peeling of the laminae, thus opening channel 12. For certain purposes, further processing can be effected within channel 12.

Returning to FIG. 1A, form-retaining member 10 is constructed of form-retaining nonliquid materials. Preferred materials are those that are readily machined, molded, or etched, that are chemically compatible—that is, do not suffer substantial degradation upon contact—with electrophoretic buffer systems, that do not appreciably bind or impede the transport of analytes through the enclosed gel, and that provide a vapor gas barrier. Usefully, form-retaining member 10 can be constructed from translucent, or transparent material, including optical quality transparent material, thus permitting strip 20 to be visualized while engaged in cavity 18. Typically, form-retaining member 10 is constructed of materials that are substantially electrically nonconducting, thus reducing or eliminating the concurrent action on strip 20 of electrical fields other than those along the channel current flow axis through cavity 18.

In typical embodiments, form-retaining member 10 is composed of ceramic, quartz, glass, silicon and its derivatives, plastic, or mixtures thereof. Among plastics useful in the construction of form-retaining member 10 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, polyester, and mixtures or copolymers thereof.

Form-retaining member 10 is also usefully composed of materials that permit heat to be conducted away from strip 20 during electrophoresis. In that regard, form-retaining member 10 can usefully be shaped to include one or more recessed regions 27, shown in FIGS. 3C and 3D, reducing the thickness of form-retaining member 10 in regions proximal to channels 12, reducing thermal resistance between strip 20 and a heat sink, usefully a fluid filled chamber, as further discussed below.

Form-retaining member 10 confers dimensional integrity upon channels 12. Dimensional integrity is important to permit the dispensing into channel 12 of rehydration solution (optionally with sample to be fractionated), to permit strip 20 to be inserted into channel 20, and to effect hydratable lodging of strip 20 in channel 12 upon rehydration.

Form-retaining member 10 can confer dimensional integrity upon channel 12 by contributing at least a portion of the circumferential wall of cavity 18 of channel 12.

For example, cavity 18 of channel 12 can be constructed as a tunnel, bore, or conduit within form-retaining member 10. In such embodiments, form-retaining member 10 contributes the entirety of the circumferential wall of cavity 18.

Alternatively, cavity 18 can be partially enclosed within form-retaining member 10, with only a portion of the circumferential cavity wall of cavity 18 contributed by member 10. In these latter embodiments, channels 12 can be machined into form-retaining member 10, or, depending on the composition of form-retaining member 10, lithographed, engraved, isotropically or anisotropically etched, milled, mechanically or chemically polished, or molded into form-retaining member 10. Alternatively, in these latter embodiments channels 12 can be fabricated on form-retaining member 10 from silicon or resin deposits or slabs.

In embodiments in which cavities 18 are not fully enclosed by inflexible member 10, channels 12 can be rendered fluidly enclosing along cavity 18 by physical attachment to form-retaining member 10 of one or more additional laminae.

Figure 4:
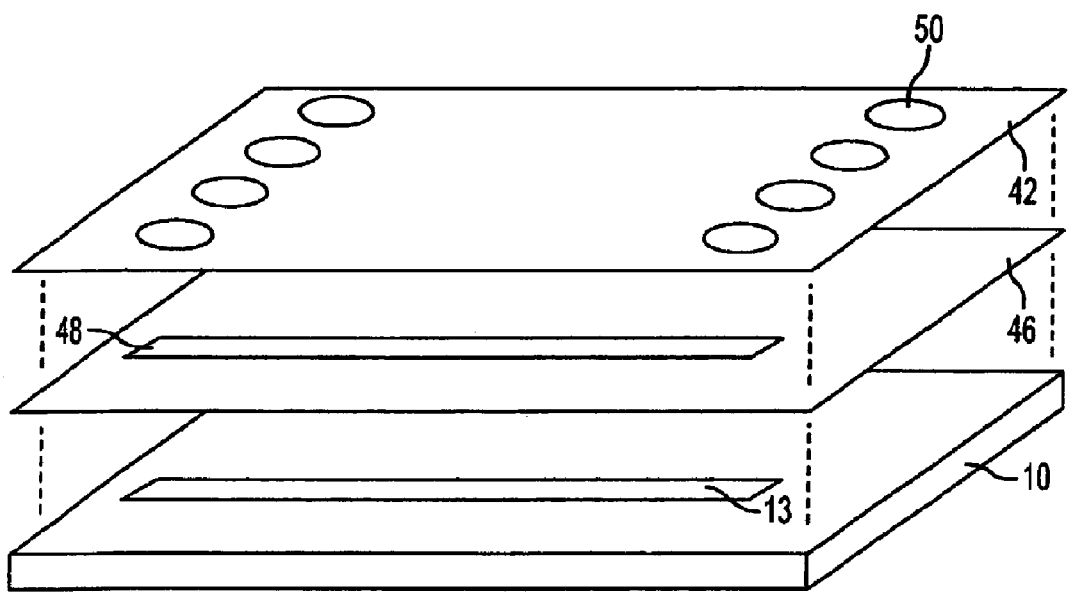
FIG. 4 is an exploded side perspective view of a multilaminate cassette of the present invention.

FIG. 4 is an exploded side perspective view of a multilaminate embodiment of cassette 100 of the present invention.

In the embodiment shown in FIG. 4, form-retaining member 10 includes depression 13. Laminate cover 42 includes a plurality of entries 50. Upon attachment of laminate cover 42 to form-retaining member 10, depression 13 becomes fluidly enclosing along cavity 18, thus completing channel 12, with entries 50 contributing to channel entries 14 and 16.

As with form-retaining member 10, laminate cover 42 can usefully be optically translucent or transparent, and is usefully substantially electrically insulating.

As with form-retaining member 10, laminate cover 42 can be composed of ceramic, quartz, glass, silicon and its derivatives, alumina, polymer, plastic, or mixtures thereof. Among plastics useful in the construction of laminate cover 42 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, polyester, and mixtures and copolymers thereof.

Laminate cover 42 can usefully be, and is often preferably, flexible. Although laminate cover 42 can be of any thickness, to confer flexibility laminate cover 42 can usefully be a film.

Laminate cover 42 can be attached to form-retaining member 10 by bonding means known in the microfabrication arts, including thermal welding, ultrasonic welding, and application of adhesives or adhesive layers.

For example, U.S. Pat. Nos. 5,800,690 and 5,699,157, incorporated herein by reference in their entireties, describe methods for completing channels by attaching planar cover elements to micromachined substrates by thermal bonding, application of adhesives, or by natural adhesion between the two components. U.S. Pat. No. 5,593,838, incorporated herein by reference, teaches that localized application of electric fields permits the meltable attachment of a cover element at about 700° C., well below the flow temperature of silicon (about 1400° C.) or of Corning 7059 glass (about 844° C.) WO 96/04547 (Lockheed Martin Energy Systems), incorporated herein by reference in its entirety, teaches that a cover plate can be bonded directly to a glass substrate after treatment in dilute $NH_4OH/H_2O_2$, followed by annealing at 500° C., well below the flow temperature of silicon-based substrates. WO 98/45693 (Aclara Biosciences), incorporated herein by reference in its entirety, discloses a thermal bonding method for fabricating enclosed microchannel structures in polymeric, particularly plastic, substrates, an adhesive method in which adhesive is applied in a film no more than 2 μm thick, and methods in which fluid curable adhesives are rendered nonflowable by partial curing before apposition of adherends.

Laminate cover 42 is usefully attached to form-retaining member 10 by reversible bonding means, thus permitting the user to separate laminate cover 42 from form-retaining member 10 after completion of electrophoresis, which in turn permits strip 20 to be removed from channel 12 for further processing. Constructing laminate cover 42 as a flexible film offers advantages in such user-mediated separation of laminate cover 42 from form-retaining member 10.

In the embodiment depicted in FIG. 4, laminate cover 42 is attached adhesively to form-retaining member 10 using double-sided laminate adhesive layer 46.

As shown, double-sided laminate adhesive layer 46 has elongate slots 48 that are congruent with depressions 13. Such slots 48 prevent contact between double-sided adhesive layer 46 and strip 20 when strip 20 is movably inserted into channel 12; contact with adhesive can interfere with movable insertion of strip 20 into cassette 100.

In multilaminate embodiments of cassette 100 in which laminate cover 42 is attached with a double-sided adhesive layer 46, the thickness of adhesive layer 46 can be adjusted to change the internal diameter of cavity 18 of channel 12, thus accommodating hydratable strip media of different thicknesses.

In alternative multilaminate embodiments of cassette 100, laminate cover 42 is itself fashioned as a form-retaining member, typically thicker than the flexible film above-described. In some of these embodiments, laminate cover 42 is fashioned as a discrete structure. In other embodiments, form-retaining laminate cover 42 and form-retaining member 10 are movably attached to one other, as by a hinge, or plurality of hinges, present therebetween. The hinge need not itself be fashioned as a separate, intermediating, structure, but can instead be fashioned as a foldable seam between form-retaining member 10 and laminate cover 42. Such seams are common in plastic cases designed to hold, e.g., drill bits.

In cases in which laminate cover 42 is form-retaining, it can be assembled to form-retaining member 10 by, e.g., snapping laminate cover 42 to form-retaining member 10. A pressure compliant surface, on form-retaining member 10 and/or laminate cover 42, facilitates sealing of the two layers, forming an enclosing member suitable for electrophoresis. Although assembly by snapping of laminate cover 42 to form-retaining member 10 has been described with particularity, any other mechanical engagement approach, such as mating of tongue and groove, insertion of a tab into a slot, etc., can also be used to similar effect.

In multilaminate embodiments of cassette 100—both those with flexible and those with form-retaining laminate covers—the internal diameter of cavities 18 can be adjusted by adjusting the depth of incursion of channel 12 into form-retaining member 10. In multilaminate embodiments of cassette 100 in which laminate cover 42 is thicker than a film, the internal diameter of cavities 18 can be adjusted additionally by adjusting the depth of incursion of channel 12 into laminate cover 42.

Channel 12 is so dimensioned—in both multilaminate and unitary embodiments of cassette 100—as to permit insertion of a prior-cast hydratable strip-based electrophoresis medium, such as an IPG strip, in its dehydrated state, and to lodgingly enclose the strip after hydration.

Immobiline DryStrip IPG strips, presently available commercially from Amersham Biosciences, (Piscataway, N.J., USA), have an approximate width of 3 mm and a depth of 0.5 mm. Accordingly, to permit electrophoresis of these commercial IPG strips, channel 12 of cassette 100 will have a width of at least about 3.0 mm, 3.1 mm, 3.2 mm, 3.3 mm, 3.4 mm, and even 3.5 mm, 3.6 mm, 3.7 mm, 3.8 mm, 3.9 mm, 4.0 mm, and even 4.1 mm, and will have depth of at least about 0.5 mm, 0.6 mm, 0.61 mm, 0.62 mm, 0.63 mm, 0.64 mm, 0.65 mm, 0.66 mm, 0.67 mm, 0.68 mm, 0.69 mm, and even 0.7 mm, 0.71 mm, 0.72 mm, 0.73 mm, 0.74 mm, 0.75 mm, 0.76 mm, and even 0.77 mm so as to movingly engage such strips in their dehydrated state and lodgingly enclose the strips when rehydrated.

ReadyStrip IPG strips, presently available commercially from Bio-Rad (Hercules, Calif., USA) have strip width of 3.3 mm and gel thickness of 0.5 mm. Accordingly, to permit electrophoresis of these commercial IPG strips, channel 12 of cassette 100 will have an approximate width of at least about 3.3 mm, 3.4 mm, and even and even 3.5 mm, 3.6 mm, 3.7 mm, 3.8 mm, 3.9 mm, 4.0 mm, and even 4.1 mm, and will have depth of at least about 0.5 mm, 0.6 mm, 0.61 mm, 0.62 mm, 0.63 mm, 0.64 mm, 0.65 mm, 0.66 mm, 0.67 mm, 0.68 mm, 0.69 mm, and even 0.7 mm, so as to movingly engage such strips in their dehydrated state and lodgingly enclose the strips when rehydrated.

In a presently preferred embodiment, suitable for electrophoresis of strips from both manufacturers, channels 12 have width of 3.7 mm and depth of 0.64 mm.

As would be expected, prior-cast hydratable electrophoretic separation media can, and likely will, be manufactured with dimensions different from those presently used. Accordingly, cassettes 100 of the present invention are not limited to those dimensioned for use with the above-described strips.

Design of the internal dimensions of channel 12, so as to permit insertion of prior-cast hydratable strip based media in their dehydrated state and lodgingly enclose the strips when rehydrated, is well within the skill in the art.

A simple test for suitability of the internal dimensions of channel 12 for a prior-cast hydratable electrophoretic separation medium 20 of any given depth and width is as follows:
(1) Position the cassette horizontally and fill channel 12 with water;
(2) Insert strip 20 through entry 14 or through entry 16 into channel 12 and advance as far as possible by hand;
(3) After 8 hours, bring cassette 100 to the vertical position and observe.

Dimensions of channel 12 are suitable if, in step (2), strip 20 can be advanced into channel 12 to a point at which less than 1 cm of strip 20 remains outside the entry chosen for insertion, and if, in step (3), air does not directly contact more than 50% of the enclosed separation medium. Strip 20 should also remain lodged within the cassette once the cassette is brought vertical in step (3).

At one end of the useable spectrum of channel dimensions, the swelling of the separation medium causes direct, occlusive, contact of the separation medium with the channel's internal wall along substantially all of the channel cavity. In this case, a visibly labeled solution (such as 0.2% w/v bromphenol blue in water) applied to the superior channel entry will be substantially precluded from the channel cavity. That is, a visibly labeled solution will typically not extend more than about 0.25 cm beyond the channel entry into the channel cavity. At the other end of the useable spectrum of channel dimensions, the swelling of the separation medium is insufficient to cause occlusive contact of the separation medium with the channel's internal wall along substantially all of the channel cavity. In this latter case, a visibly labeled solution such as 0.2% w/v bromphenol blue in water will enter the channel cavity from the superior entry when the cassette is brought vertical. In neither case, however, will air contact more than 50% of the enclosed separation medium.

An additional, functional test for suitability of the internal dimensions of channel 12 for a prior-cast hydratable electrophoretic separation medium of given dimensions is to replace step (3) of the test set forth above with an actual electrophoresis experiment; dimensions of channel 12 are suitable if, in step (2), strip 20 can be advanced into channel 12 to a point at which less than 1 cm of strip 20 remains outside the entry chosen for insertion, and if, after electrophoresis, adequate electrophoretic separation is achieved.

If strip 20 is an IPG strip, this latter test may usefully be performed as follows.

Mix 5.0 μL of Serva IEF standard (catalogue no. 39212-01, Serva Electrophoresis GmbH, Heidelberg, Germany) with sufficient rehydration buffer of the following composition to fill the channel: 8.0 M urea, 0.5% ampholytes (3-10 IPG buffer, cat. no. 17-6001-11, Amersham Biosciences), 2.0% (w/v) CHAPS, 20 mM DTT, 0.0025% (w/v) bromphenol blue. Pipette the solution into a channel of the cassette with the cassette positioned horizontally. Insert the strip into the channel so that about 3 mm overextends the channel entries. Occlude the channel entries with cover tape and allow the strip to rehydrate for 8-16 hours. Remove cover tape and, if present, loading wells.

Apply an electrode wick (further described below) to each set of entries. Evenly apply 750 µl of deionized water to each electrode wick.

Contact the cassette to the electrodes of a buffer core (further described hereinbelow). Apply a buffer dam (further described below) to the other contact face of the buffer core. Slide the buffer core into an electrophoresis chamber and fill the outer chamber surrounding the buffer core with water. Take care that the water does not overtop the cassette and spill into the inner chamber (the outer walls of which are defined by the cassettes and buffer core).

Apply a voltage in three steps according to the following profile: 200 V for 20 min, 450 V for 15 minutes, 750 V for 15 minutes, 2000 volts for 30 minutes.

Channel dimensions are suitable if discrete marker bands are observable.

Figure 2:
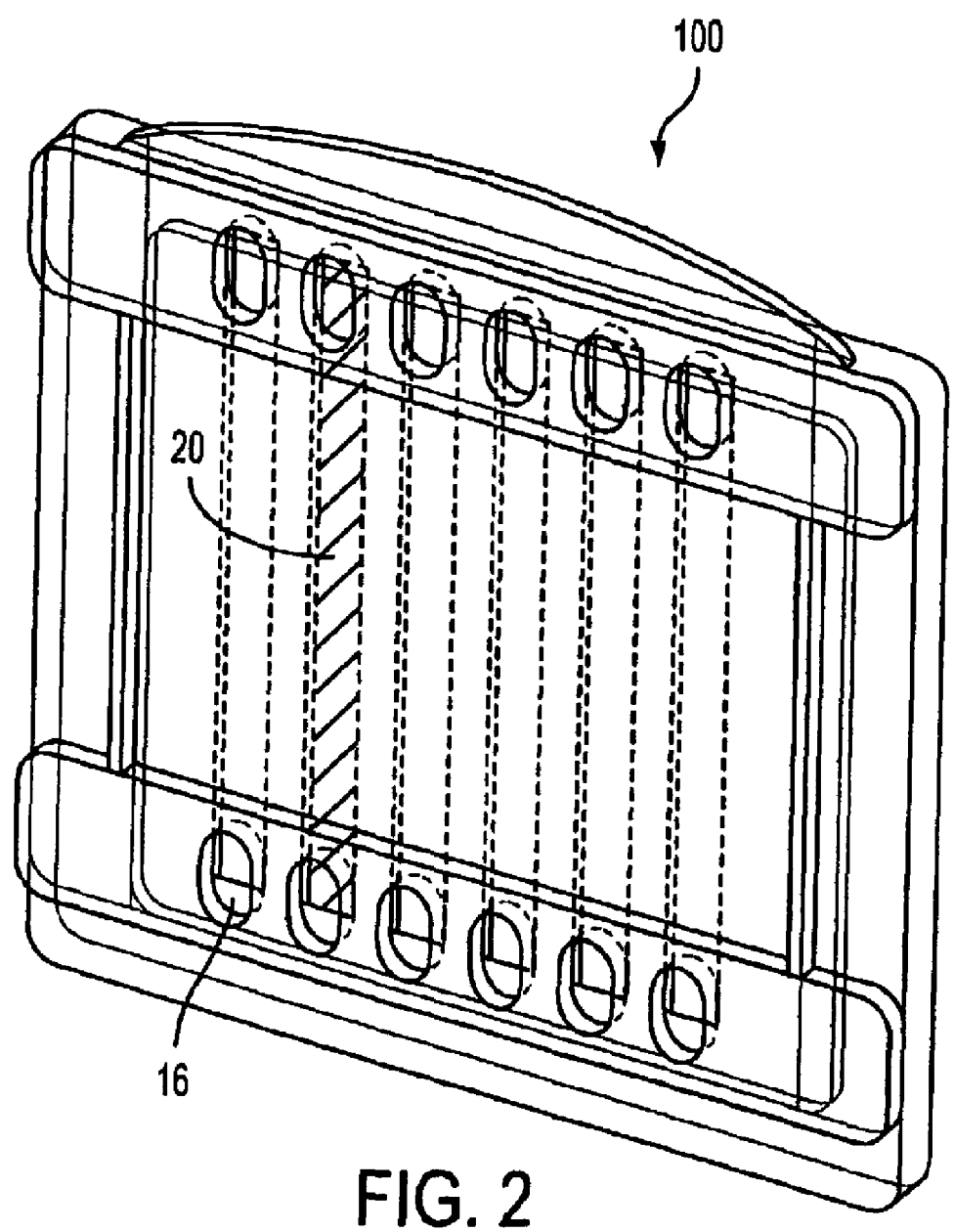
FIG. 2 is a front perspective view of a cassette of the present invention with an IPG strip inserted into one of six available channels.

Channel entries 14 and 16 will typically, but not invariably, be spaced so that channel 12 engages substantially the entire length of strip 20, as shown e.g. in FIG. 2.

IPG strips are currently available commercially in a variety of lengths. For example, Immobiline DryStrip IPG strips, presently commercially available from Amersham Biosciences, (Piscataway, N.J., USA), are available with gel lengths of 70 mm, 110 mm, 130 mm, 180 mm, and 240 mm. ReadyStrip IPG strips, presently commercially available from Bio-Rad (Hercules, Calif., USA), are available with gel lengths of 70 mm, 110 and 170 mm. ZOOM® IPG strips presently commercially available from Invitrogen (Carlsbad, Calif., USA) have gel lengths of 70 mm.

Thus, in certain presently preferred embodiments of cassette 100 of the present invention, channels 12 are fashioned to accommodate substantially the entire length of strips with gel lengths of 70 mm, 110 mm, 170 mm, 180 mm, and 240 mm in length.

In such commercial IPG strips, the polyester backing typically extends for some distance beyond the gel on either end. Thus, channels 12 will typically have length at least as long as the stated gel length (70, 100, 170, 180, or 240 mm), typically with extension of 1 mm, 2 mm, 3 mm, 4 mm, 5 mm, or even 6 mm on both ends. Thus, for an IPG strip of nominal 70 mm gel length, channel 12 will be at least about 70 mm in length, 72 mm in length, 74 mm in length, 76 mm in length, 78 mm in length, and even 80 or 82 mm in length. In a presently preferred embodiment for IPG strips of 70 mm stated gel length, channel 12 will be 80 mm in length.

It would be expected that rehydratable strip-based separation media will in the future be available in a variety of lengths, just as they are expected to be available in a variety of widths and depths, as described above. It is, therefore, an aspect of the invention to provide cassettes 100 with channels 12 dimensioned to engage prior-cast hydratable electrophoretic separation media of any chosen length.

As suggested above, significant overextension or underextension of channel 12 by strip 20 is undesirable.

For example, if strip 20 extends substantially beyond entry 14, entry 16, or both, the overextending portion(s) of strip 20 will be exposed to atmospheric $CO_2$, obviating an important advantage of the present invention. Furthermore, the overextending portion(s) of strip 20 can permit leakage of ampholyte and/or protein from the strip. Additionally, only that portion of the separation medium lying between the spaced electrical connections will be functionally available for separation, reducing the functional portion of gel. Finally, the overextending portion(s) might interfere mechanically with establishment of electrical communication properly required for electrophoresis. And when strip 20 underextends channel 12, it can prove difficult to establish effective electrical communication with the enclosed strip.

To accommodate these difficulties in a cassette having channels of nonoptimal length, if strip 20 overextends channel 12, excess can be removed using scissors or knife; typically, only that portion of strip 20 lacking separation media will be so removed. If strip 20 underextends channel 12, the recessed end can be brought into effective electrical communication with the exterior of channel 12 by filling the recessed end with an electrically conductive, channel-filling, material.

Among materials usefully employed to bring the underextended end of strip 20 into electrical communication with an entry 14 or 16 of cassette 100 are materials that can be applied in liquid or semiliquid state, in which state they can conform in shape to the channel interior, and that thereafter polymerize or gel into a shape-holding phase.

Usefully, the material can be a polymer gel, such as agarose. When so used, the agarose can be rendered molten in the presence of electrolyte-containing buffer, such as rehydration solution, applied to entry 14, entry 16, or both as a molten liquid, and thereafter allowed spontaneously to gel with decrease in temperature. Polyacrylamide can also be used, although in this latter case polymerization of monomers and cross-linkers must be effected by addition of catalyst, as is well known in the art.

Usefully, cassette 100 includes a plurality of channels 12. In cases in which cassette 100 includes a plurality of channels 12, the current flow axes of plural channels 12 are usefully substantially parallel to one another, and cavities 18 of plural channels 12 are fluidly noncommunicating with one another except at channel entries 14 and 16.

In such embodiments, channels 12 need not have identical cavity 18 dimensions, a single cassette 100 thus accommodating strips 20 of different dimensions. Typically, however, cavities 18 of plural channels 12 will all have the same internal dimensions.

Although cassette 100 is described above as permitting user-directed insertion of strip 20 into channel 12, it is another aspect of the present invention to provide a cassette, as above-described, in which strips 20 have already been inserted during manufacture. Such cassettes 100 can usefully be disposable.

To facilitate sample application, and in particular to facilitate sample application without cross contamination as among plural channels 12, cassette 100 can usefully include loading wells. FIG. 1A shows one embodiment of such loading wells; FIGS. 1B and 1C show another embodiment of such loading wells.

With reference to FIG. 1A, cassette 100 is shown to have two well-forming members 22. The two well-forming members define discrete reservoirs, termed loading wells, at each of the six entries 14 and six entries 16, respectively. When cassette 100 is horizontal with well-forming members 22 superior to form-retaining member 10, each loading well can maintain a defined maximum volume of fluid in contact with an entry 14 (or entry 16) without cross-over fluid contact with adjacent entries.

In cases in which sample to be fractionated is applied after insertion of strip 20, the loading wells permit samples of volume less than the maximum reservoir volume to be applied discretely to individual wells 14 (and/or 16) without cross-over contamination. In cases in which sample is applied in rehydration buffer prior to insertion of strips 20 into channels 12, the loading wells prevent cross-over contamination by sample displaced from channel 12 during strip insertion.

After sample to be fractionated (such as a protein sample for isoelectric focusing on IPG strips) enters the separation medium of strip 20, cross-over contamination among channels 12 is usually foreclosed, even if entries 14 are thereafter placed in fluid communication with one another and entries 16 are thereafter placed in fluid communication with one another. Accordingly, well-forming members 22 can be removable. Such removal can facilitate subsequent application of conductive wicks 24, as shown in FIG. 3B and further described below.

Because well-forming member 22 is typically removed prior to electrophoresis, there are fewer constraints on the materials from which it can be constructed than for form-retaining member 10 and, in multilaminate embodiments of cassette 100, for laminate cover 42. Indeed, well-forming member 22 can be constructed of any material that is substantially chemically unreactive with the rehydration solution, such as ceramic, quartz, glass, silicon and its derivatives, plastic, natural or synthetic rubber polymers, or mixtures thereof Among plastics useful in the construction of well-forming member 22 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, and mixtures thereof. Silicone and its derivatives are also useful.

In certain embodiments, well-forming member 22 can be composed of electrically conductive materials; this facilitates "active rehydration" of strip 20. In "active rehydration", strip 20 is rehydrated in the presence of a low voltage gradient, approximately 100 V, established along the channel current flow axis of strip 20 between entries 14 and 16.

In cases in which active rehydration is desired, well-forming member 22 can be composed of an electrically-conductive material, such as an electrically-conductive polymer, such as a polymer impregnated or doped with carbon. After both strip 20 and rehydration solution are applied to channel 12 (in either order), a cathode is contacted to first conductive well-forming member 22 and an anode is contacted to second conductive well-forming member 22 and a voltage applied during the rehydration period. The anode and cathode can be, e.g., an electrode bar, such as is found on the MultiPhor (Amersham Biosciences, Piscataway, N.J.) or Blue Horizon (Serva, Heidelberg, Germany) devices.

When cassette 100 is unitary—that is, having channels 12 formed completely within form-retaining member 10—well-forming members 22 can be attached to form-retaining member 10. When cassette 100 is, instead, multilaminate—e.g., with channels 12 formed in part by a laminate cover 42—well-forming members 22 can be attached to laminate cover 42, as shown in FIG. 5.

Figure 5:
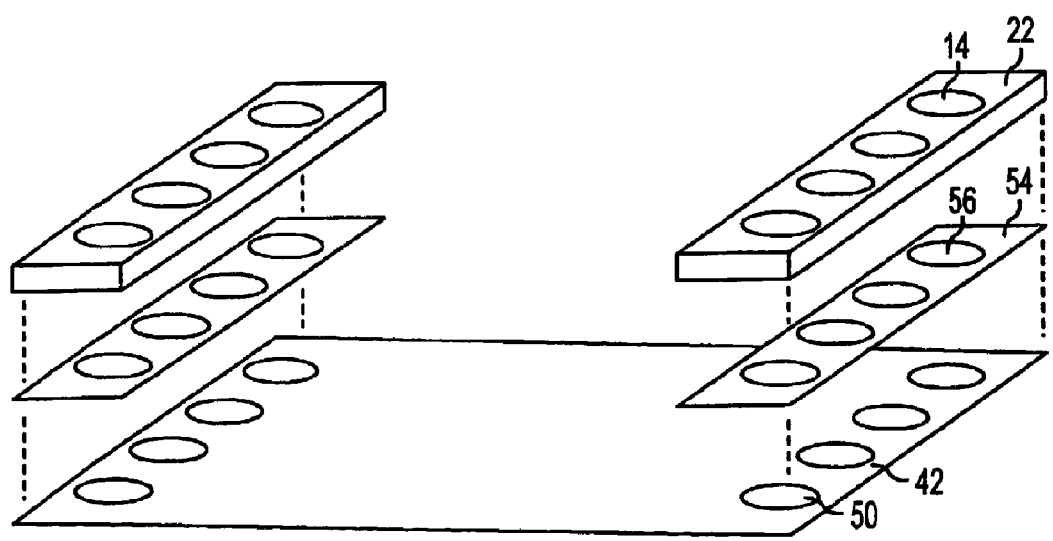
FIG. 5 is an exploded side perspective view of a loading well assembly of a cassette of the present invention.

FIG. 5 is an exploded side perspective view showing well-forming members 22 attached adhesively to laminate cover 42 using double-sided well-forming member adhesive layer 54. However, as described above with respect to attachment of laminate cover 42 to form-retaining member 10, which discussion is incorporated herein by reference, well-forming member 22 can be attached to laminate cover 42 by a variety of bonding means well known in the microfabrication arts, including thermal welding, ultrasonic welding, and application of liquid or partially cured adhesives, as well as by means of adhesive layers.

Well-forming member 22 can in the alternative be attached to laminate cover 42 by engagement of opposing, matching surfaces, as in a snap, or engagement of tongue with groove, or engagement of tab with slot.

However bonded, well forming members 22 will usefully be reversibly attached to cassette 100, thus permitting removal of the well-forming members prior to electrophoresis. In cases in which attachment is by means of a double-sided well-forming member adhesive layer 54, the adhesive layer is usefully designed to adhere more strongly to form-retaining member 10 (or, in multilaminate embodiments, to laminate cover 42) than to well-forming member 22; in such adhesively biased embodiments, removal of well-forming member 22 will typically leave adhesive layer 54 on form-retaining member 10 (or laminate cover 42), facilitating application of conductive wicks, as further described below.

Figure 3A:
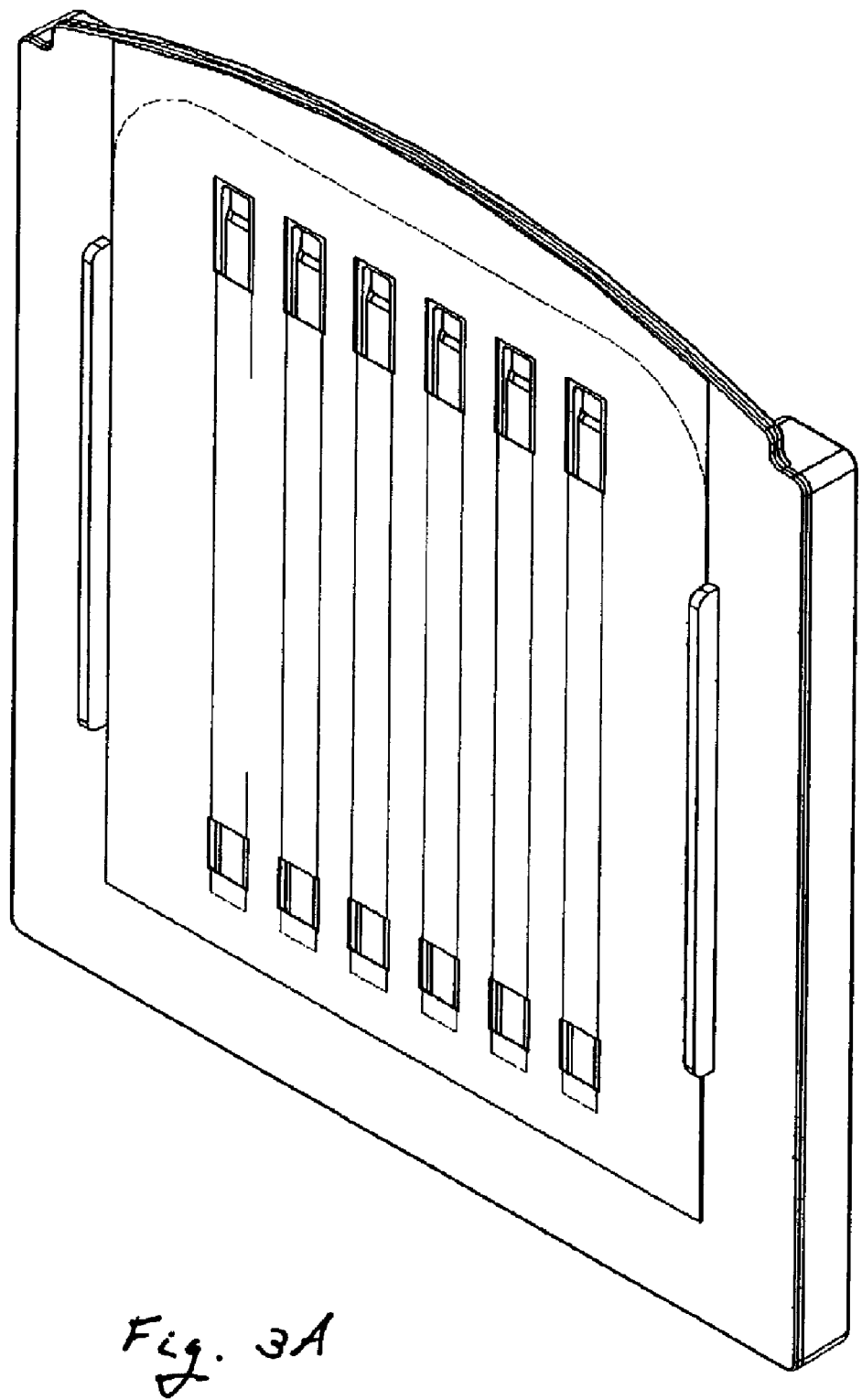
FIG. 3A is a front perspective view of a cassette of the present invention, with well-forming member removed, prior to application of a conductive wick.
Figure 3B:
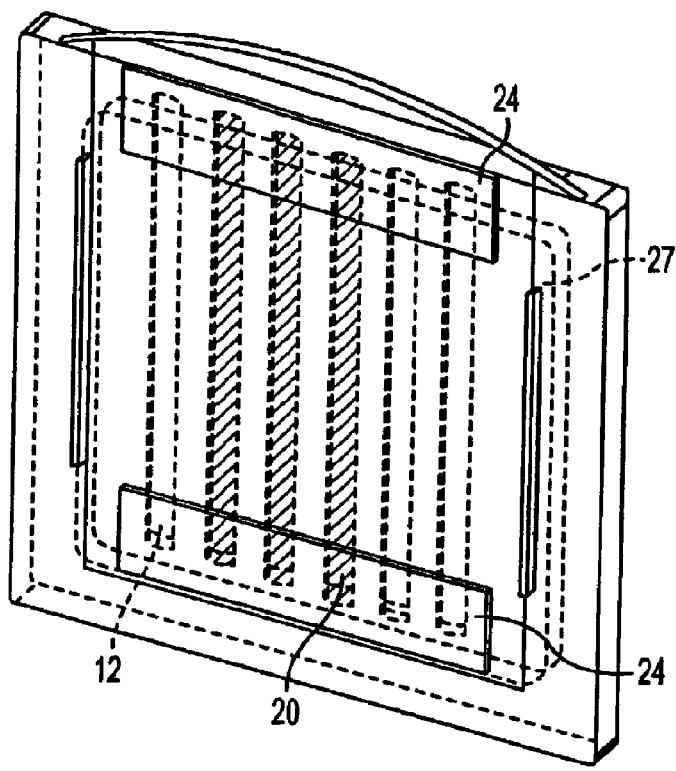
FIG. 3B is a front perspective view of a cassette of the present invention with a first conductive wick contacting the anodic end of IPG strips present in three of six available channels and a second conductive wick contacting the cathodic end of the three IPG strips.
Figure 3C:
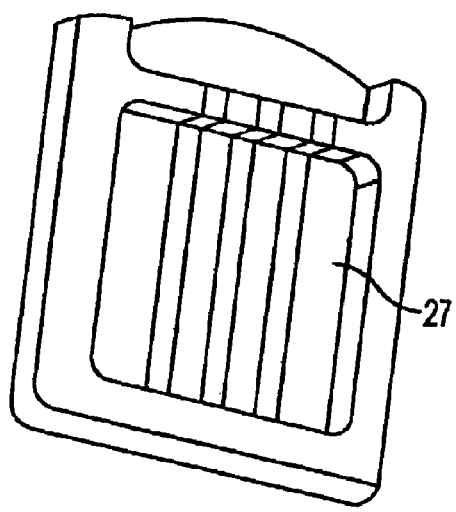
FIG. 3C is a back perspective view of an embodiment of a cassette of the present invention, particularly showing a recessed region that facilitates heat dissipation during electrophoresis.
Figure 3D:
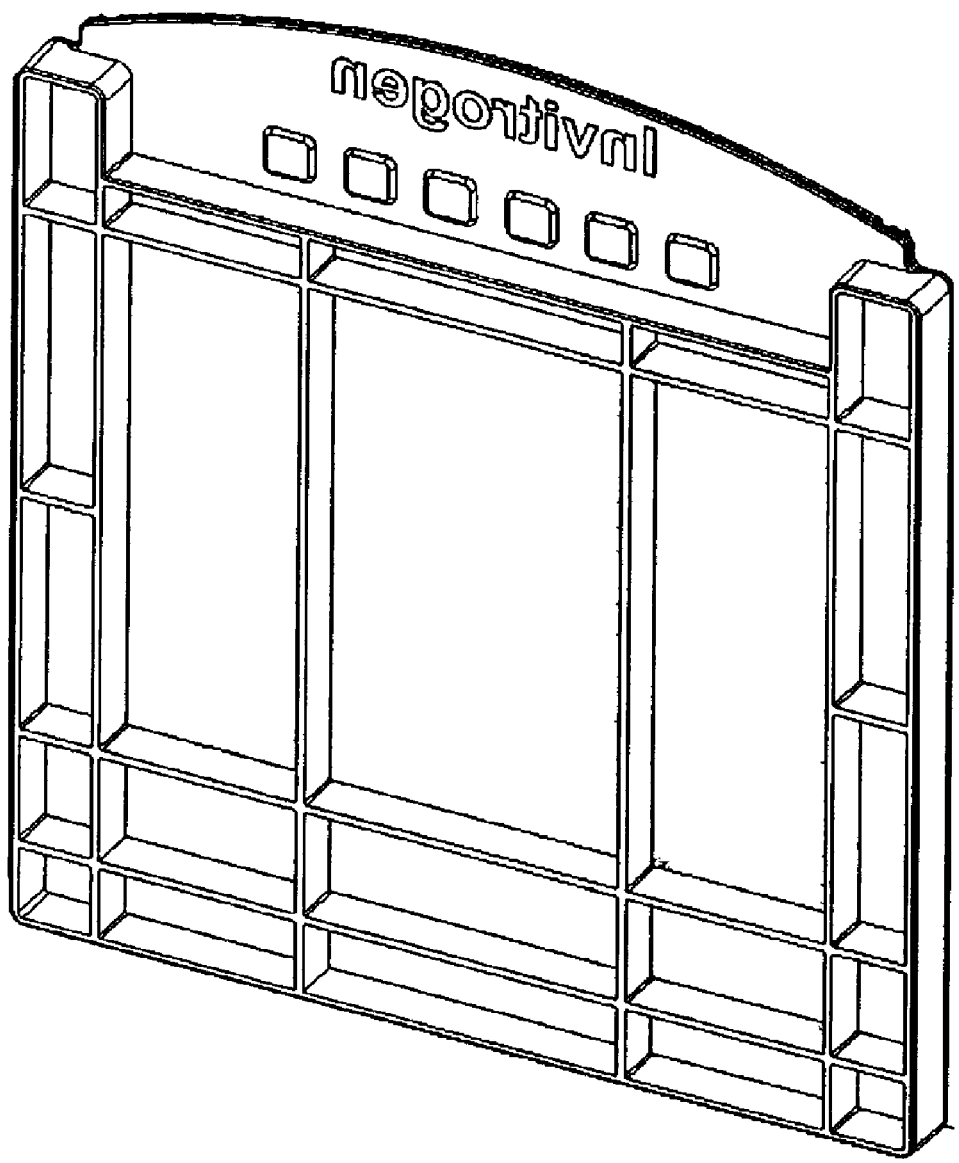
FIG. 3D is a back perspective view of another embodiment of a cassette of the present invention, particularly showing a plurality of recessed regions that facilitate heat dissipation during electrophoresis.

FIG. 3A shows an embodiment of the cassette of the present invention with well-forming members 22 removed, prior to application of conductive wicks, as further described below.

Although cross-contamination of samples as among plural channels 12 will typically be foreclosed by entry of sample into the separation medium of strip 20, thus obviating the requirement for continued presence of well-forming members 22 during electrophoresis, it can nonetheless be advantageous further to seal entries 14 and/or 16 after sample application.

In these latter embodiments, sealing is accomplished by application to entries 14 and/or 16 of a material that is electrically conductive, that can be applied in a state in which it conforms in shape to the entry and/or loading well, and that thereafter polymerizes or gels into a shape-holding phase. As above, such material can usefully be a polymer gel, such as agarose or acrylamide.

In particularly useful approaches, entries 14 and/or 16 are sealed with an amount of material sufficient to fill channel 12 and entry 14 (and/or entry 16) to a level flush with the surface of form-retaining member 10. Such geometry facilitates electrical contact of the anodic and cathodic ends of strip 20 directly or indirectly with anode and cathode electrodes.

Returning to FIG. 1A, cassette 100 can optionally, and usefully, include ribs 40.

Ribs 40 facilitate alignment of laminate cover 42 and well-forming members 22 during manufacture of cassette 100. Ribs 40 can also facilitate proper operational engagement of cassette 100 by an electrophoresis chamber or buffer core, as further described below.

Ribs 40 can be machined or molded directly from form-retaining member 10, or can be separately constructed and fixed thereto. When separately constructed, ribs 40 are usefully constructed of solid or semisolid materials that are readily machined, molded, or etched, and that are chemically compatible—that is, do not suffer substantial degradation upon contact—with electrophoretic buffer systems. Usefully, ribs 40 can be constructed of materials that are substantially electrically insulating, including ceramic, quartz, glass, silicon and its derivatives, or plastic, or mixtures thereof. Among plastics useful in the construction of ribs 40 are polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, polystyrene, polyacrylonitrile, polyurethane, polyamides, polyaniline, polyester, and mixtures and copolymers thereof.

As noted above, after rehydration of and introduction of sample into strip 20, strip 20 becomes lodgingly enclosed in cavity 18 of channel 12. With strip 20 so enclosed, electrophoresis can then be performed, without removing strip 20 from cassette 100, by applying a voltage gradient to flow current through strip 20 along the channel current flow axis sufficient to effect electrophoretic separation of analytes therein.

FIG. 3B illustrates one useful, but nonlimiting, approach by which cassette-enclosed strip 20 is rendered contactable by cathode and anode electrodes to complete the necessary electrical circuit.

FIG. 3B is a front perspective view of a cassette of the present invention having six channels 12. As shown, a first conductive wick 24 contacts strips 20 (present in three of six available channels 12) at entries 14; a second conductive wick 24 contacts strips 20 at entries 16.

Wick 24 includes an electrically conductive material. The material need not be constitutively conductive: it suffices, and indeed typically will be the case, that wick 24 is conductive when wet. In this latter case, wick 24 can usefully be composed of a bibulous material, such as paper, nitrocellulose, felt, nylon, or derivatives thereof.

As described above, as an alternative or in addition to the presence of wicks 24, strip 20 can be electrically coupled to cathode and anode electrodes through intermediation of electrically conductive polymers or hydrogels such as agarose.

As shown in FIG. 3B, first conductive wick 24 can usefully contact each of plural entries 14, and second conductive wick 24 can usefully contact each of plural entries 16, facilitating application of current in parallel to plural channels 12. While useful, such geometry is not required.

First conductive wick 24 is then contacted with an electrode, serving as either cathode or anode. The choice as between applying a cathode or anode to wick 24 depends upon the intended electrophoretic technique, the location of sample application, and other conditions well known to those in the electrophoretic arts. For example, for isoelectric focusing using IPG strips, where one end of the strip is acidic and the other basic, the basic end of the strip is preferably placed in electrical communication with the cathodic electrode.

Second conductive wick 24 is then contacted with an electrode (an anode if first wick 24 is contacted with the cathode, a cathode if first wick 24 is contacted with the anode).

Any means of electrode attachment to wicks 24 can be used, as long as effective electrical communication is established.

In an alternative to use of conductive wicks 24, spaced electrical communication with enclosed strip 20 can be effected by direct contact of strip 20 with anode and cathode electrodes. Contact can be accomplished by passage of anode and cathode electrodes through entries 14 or 16, or alternatively by passage of electrodes through form-retaining member 10 or laminate cover 42 elsewhere than at entries 14 and/or 16. As an example of the latter approach, electrodes shaped as blades can be used to pierce laminate cover 42 in embodiments in which laminate cover 42 is a flexible film, thereby contacting enclosed strip 20 at spaced intervals.

Electrophoresis can thereafter be conducted with cassette 100 in any physical orientation. In a particularly useful approach, electrode contact is effected using an adaptor that permits electrophoresis to be conducted with cassette 100 maintained vertically; even when cassette 100 is held vertical, channels 12 of cassette 100 can be horizontal or vertical, as desired.

Returning to FIG. 3B, it is, therefore, another aspect of the invention to provide an adaptor that permits cassettes 100 of the present invention, within which are lodgingly enclosed strips 20, to be electrophoresed in a vertical direction. It should be noted that even when cassette 100 is itself oriented vertically, channels 12 can still be oriented horizontally; in such an orientation, channels 12 of cassette 100, if present plurally, would be spaced with vertical offset from one another. For clarity, therefore, the term "vertical" is intended to refer to the orientation of the cassette, not the channels.

Electrophoresis of cassette 100 in the vertical dimension has the significant advantage of reducing the bench footprint of the electrophoresis device, freeing up valuable bench space for other equipment or uses.

Furthermore, modular electrophoresis systems for performing slab gel electrophoresis in the vertical dimension are well known, see e.g. U.S. Pat. Nos. 5,888,369 and 6,001,233, and are commercially available (Invitrogen, Carlsbad, Calif., USA; Bio-Rad, Hercules, Calif., USA). In preferred embodiments, the adaptor of the present invention permits cassettes 100 of the present invention to be electrophoresed in such existing modular electrophoresis systems, permitting the efficient use of such prior-purchased equipment for electrophoresis of prior-cast hydratable electrophoretic separation media, such as IPG strips.

Figure 6A:
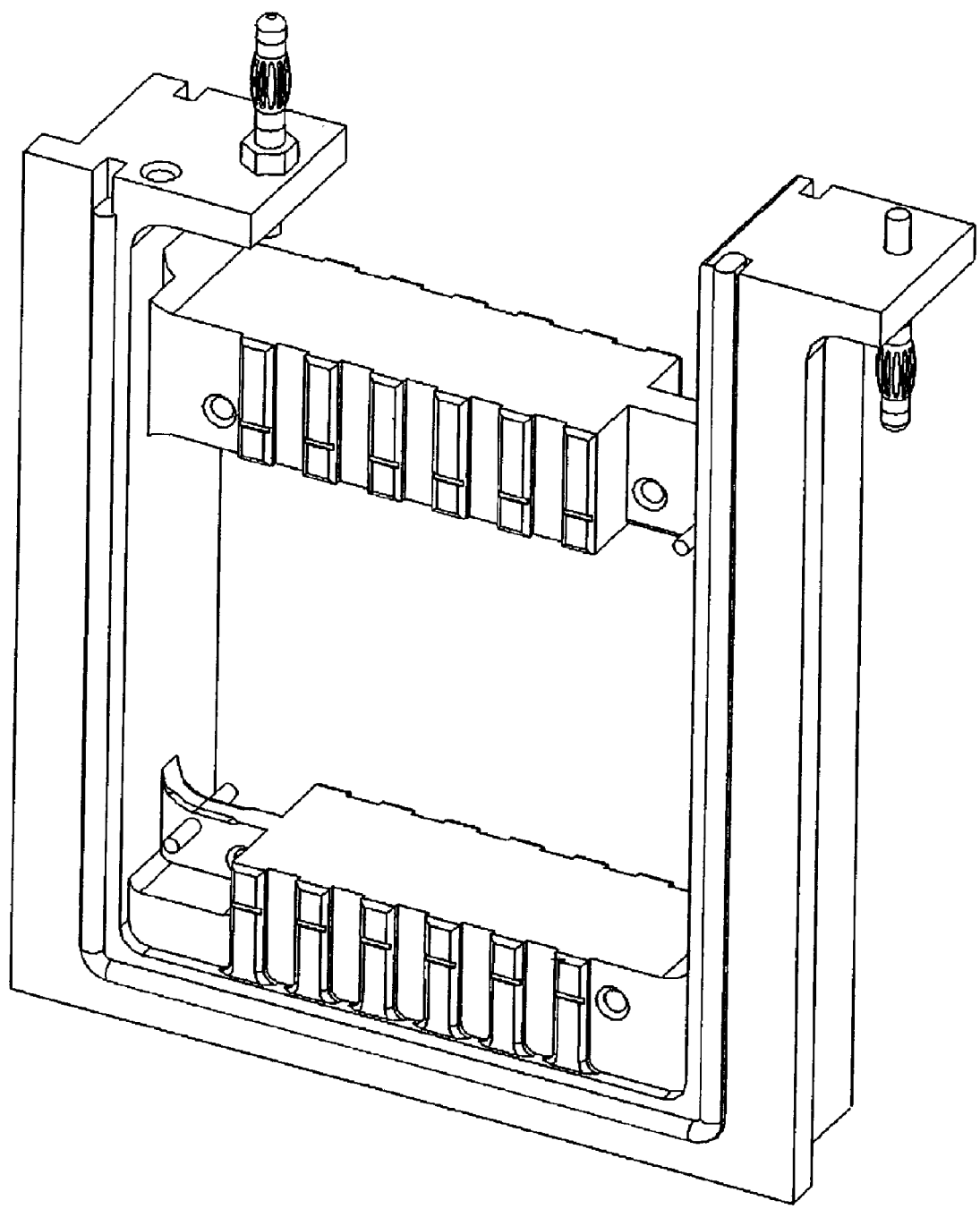
FIG. 6A is a front perspective view of a buffer core of the present invention, without anode electric wire or cathode electric wire, with gasket.
Figure 6B:
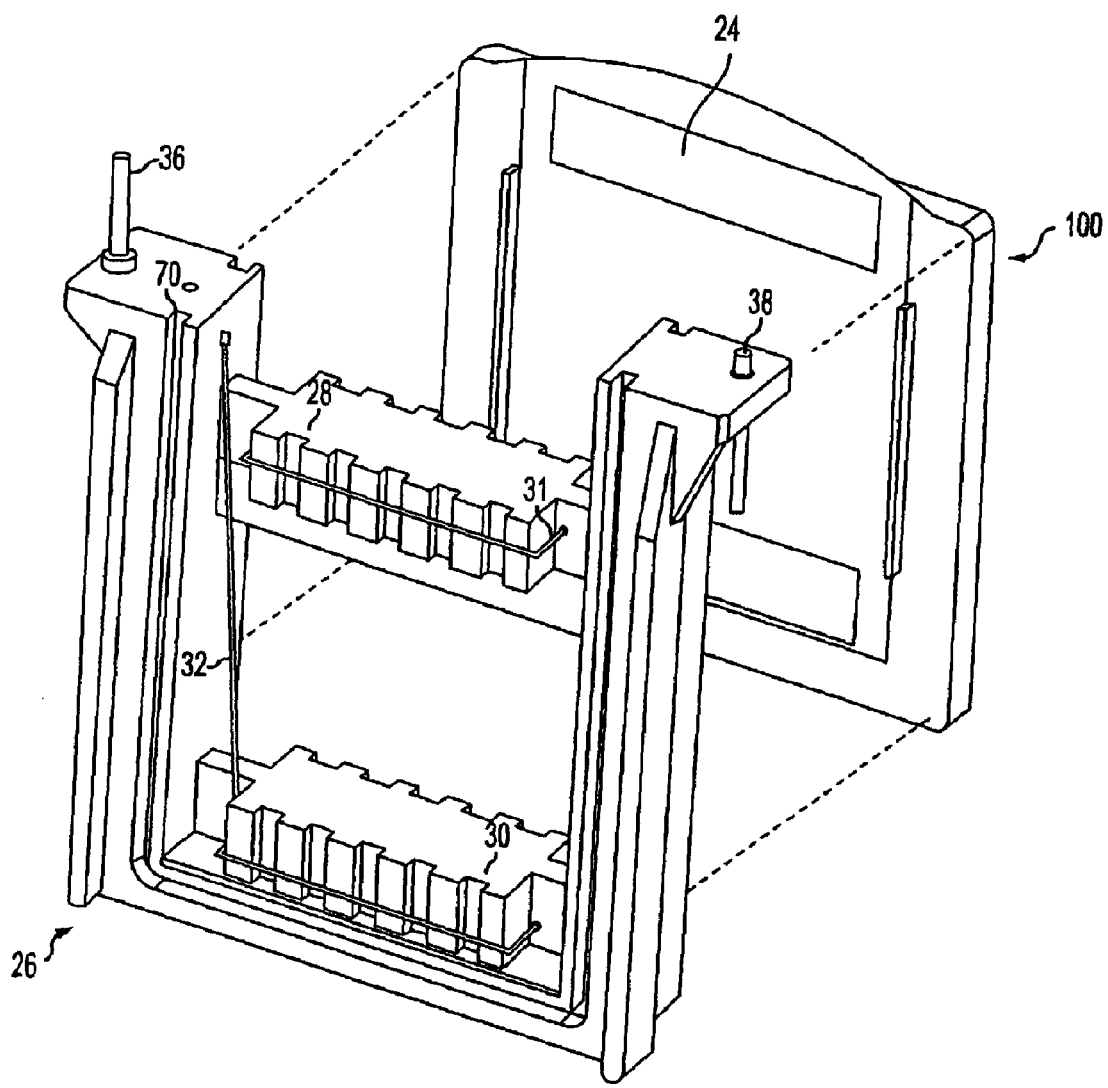
FIG. 6B is a front perspective view of a buffer core of the present invention (front) operationally aligned to contact its anode and cathode electrodes respectively to anodic and cathodic wicks of a cassette of the present invention (rear)
Figure 6C:
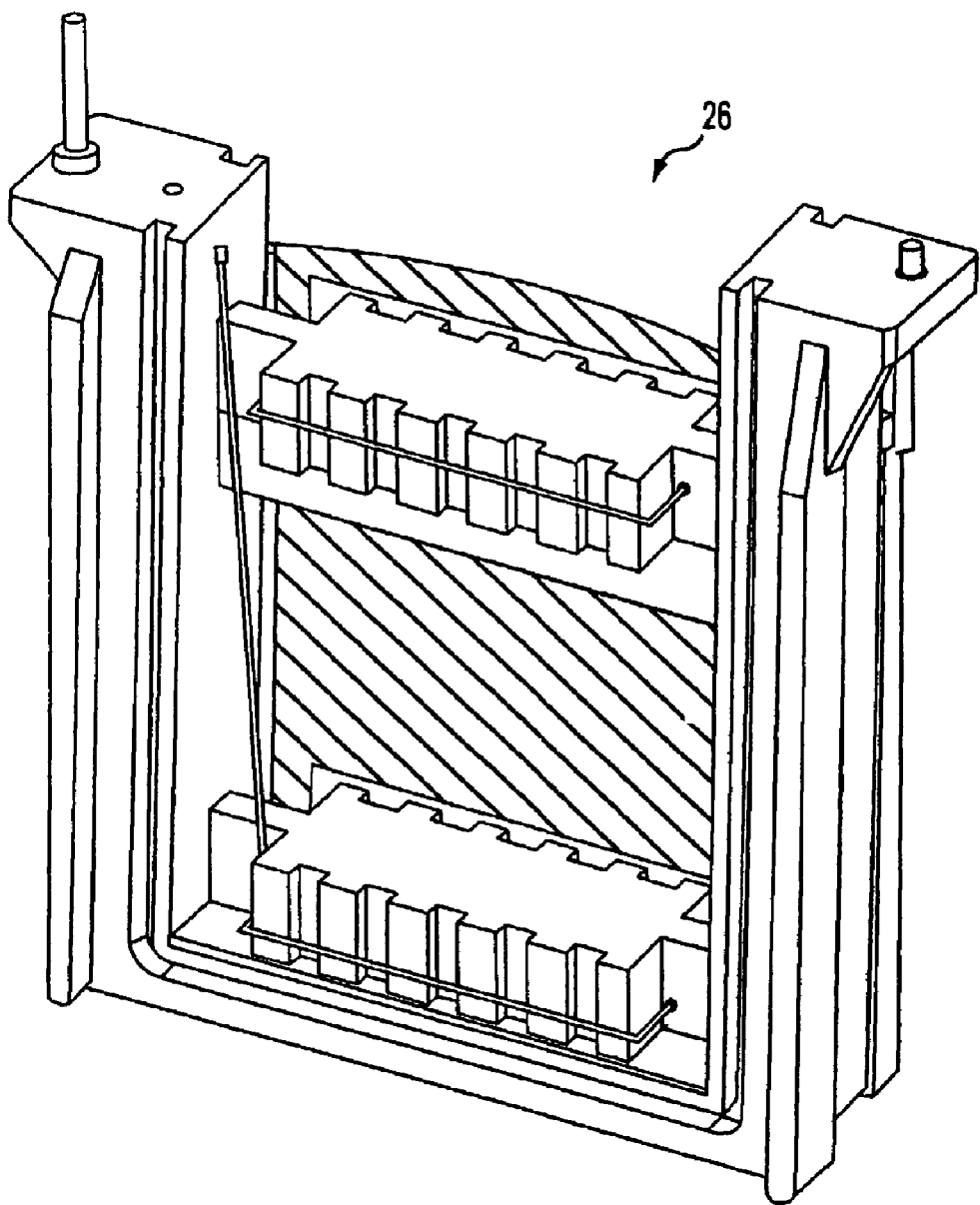
FIG. 6C is a front perspective view of the buffer core and cassette of FIG. 6B in operational contact with one another.

FIG. 6A is a front perspective view of an adaptor, herein termed a buffer core, of the present invention. FIG. 6B is a front perspective view of the buffer core (front) operationally aligned with, but not yet contacting, a cassette of the present invention (rear); operational contact is shown in FIG. 6C. As can be seen, buffer core 26 is designed simultaneously to align cathode electrode wire 31 with cathodic wick 24 of cassette 100 and anode electrode wire 32 with anodic wick 24 of cassette 100.

As shown in FIG. 6B, cathode wire 31 is attached at a first end to cathode contact prong 38; analogously, anode wire 32 is attached at a first end to anode contact prong 36. Contact prongs 38 and 36 permit the removable attachment of wires having standard female gender plugs; as is well known in the electrophoresis arts, the other end of such wires is typically connected to a power supply, such as a regulatable power supply.

Also as shown, cathode wire 31 extends from cathode contact prong 38 to support 28 before terminating at a second end, and anode wire 32 extends from anode contact prong 36 to support 30 before terminating at a second end. Supports 28 and 30 are typically composed of materials that are substantially electrically insulating and substantially inert to electrophoresis running buffers. For example, supports 28 and 30 are conveniently made of plastic, such as polycarbonate.

Contact between anode wire 32, cathode wire 31, and their respective wicks 24 of cassette 100 is effected by application of an external compressive force applied inwardly against cassette 100. The anode and cathode wires are thereby compressed between their respective support and wick, establishing an electrical connection.

Figure 6D:
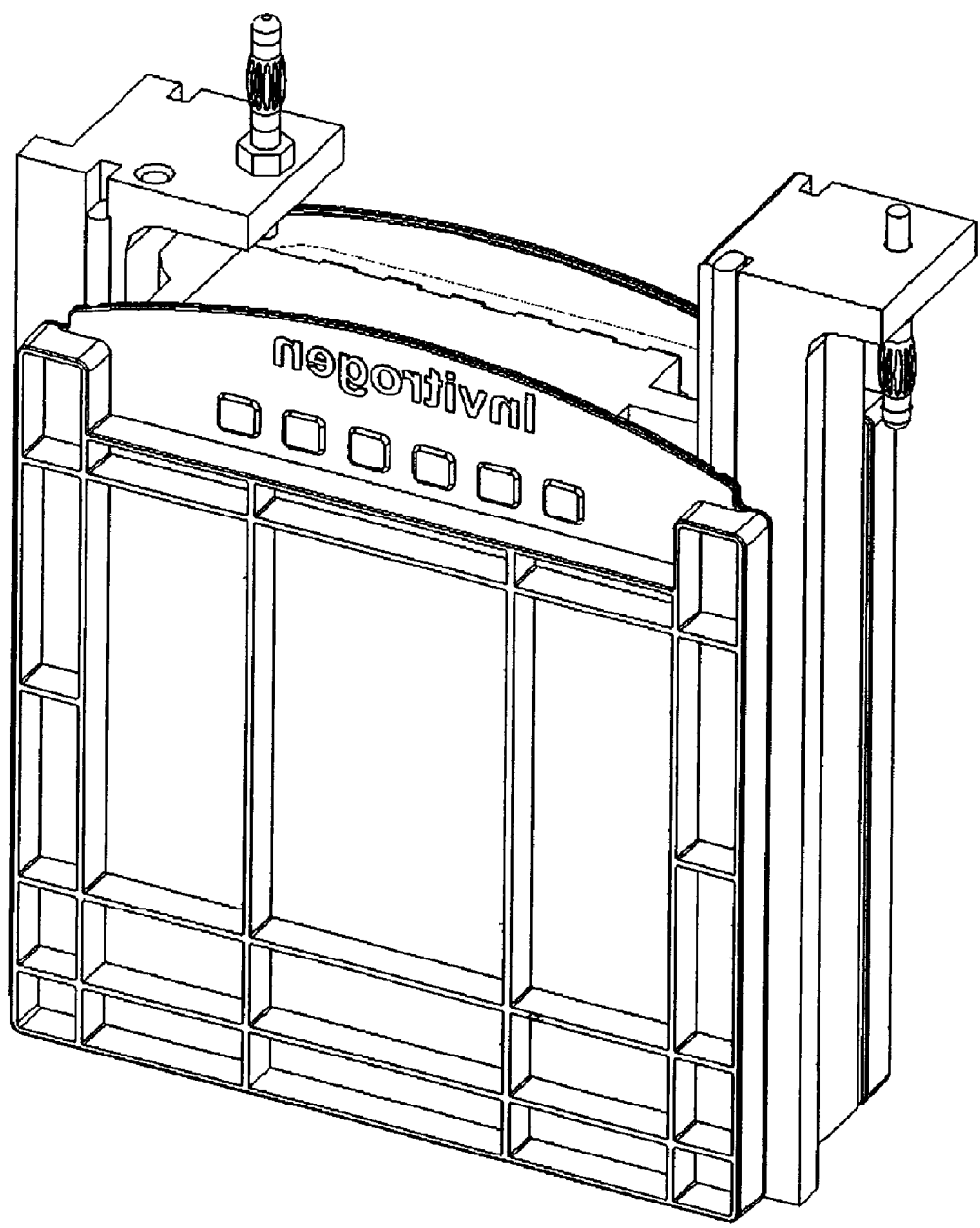
FIG. 6D is a front perspective view of a buffer core in operational contact with two cassettes of the present invention.
Figure 6E:
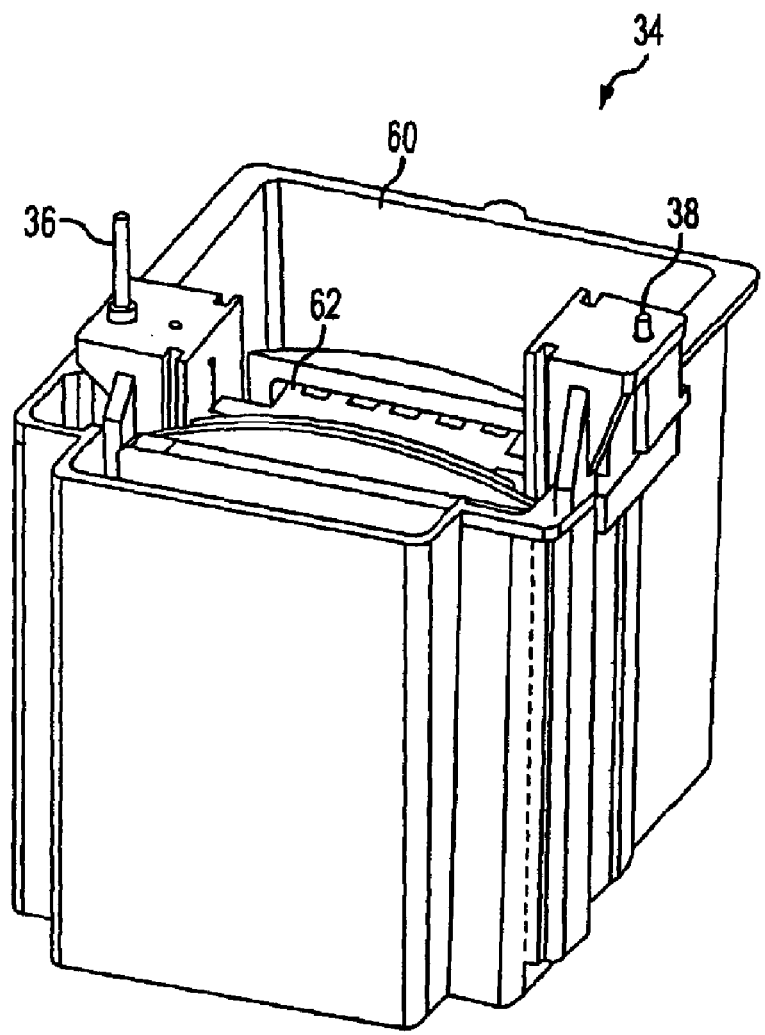
FIG. 6E shows a buffer core of the present invention, with cassettes of the present invention operationally engaged thereupon, further engaged in an electrophoresis chamber.

As shown in FIG. 6D, buffer core 26 can, and typically will, be operationally aligned and contacted simultaneously with a second cassette 100. So aligned and so contacted, buffer core 26 and cassettes 100 define an internal chamber 62, open only at the top and sealed, except from above, from external liquids. If the number of strips needed to be electrophoresed can be accommodated in a single cassette, a "buffer dam", dimensioned similarly to cassette 100 but lacking channels 12 can be used to complete buffer core internal chamber 62.

In order to conduct electrophoresis using cassettes and buffer cores of the present invention, cassettes 100 (or singular cassette 100 and a buffer dam) are aligned and contacted to buffer core 26. The assembly is then engaged in electrophoresis buffer chamber 34 which itself, or in conjunction with an additional device, urges cassettes 100 (or singular cassette 100 and buffer dam) into sealable contact with buffer core 26. Such additional urging device can be a cam-activated clamp ("tension wedge"), as further described in U.S. Pat. No. 6,001,233, incorporated herein by reference in its entirety.

Alternatively, buffer core 26 is first loosely engaged in electrophoresis buffer chamber 34, and cassettes thereafter aligned, contacted to, and then further urged against buffer core 26.

Fluid-tight contact between buffer core 26 and cassettes 100 (or singular cassette 100 and buffer dam) is typically, but optionally, further facilitated by a gasket, such as a silicone gasket, fitted into groove 70 of buffer core 26, shown in FIGS. 6A and 6D.

As noted above, buffer core 26 and cassettes 100 (or singular cassette 100 and a buffer dam) in sealed engagement therewith define internal chamber 62. This chamber isolates cathode wire 31 and anode wire 32 from fluids present external to buffer core 26 in electrophoresis chamber 34 (chamber 60), so long as the fluid level in electrophoresis chamber 60 does not over top cassettes 100.

Accordingly, electrophoresis chamber 34 can be filled with any chosen liquid solution, to a level that does not overtop cassettes 100, without affecting the electrical circuit. Such fluids can thus usefully serve as a heat sink, reducing the temperature of strips 20 as they are subjected to current flow in cassettes 100.

Figure 11:
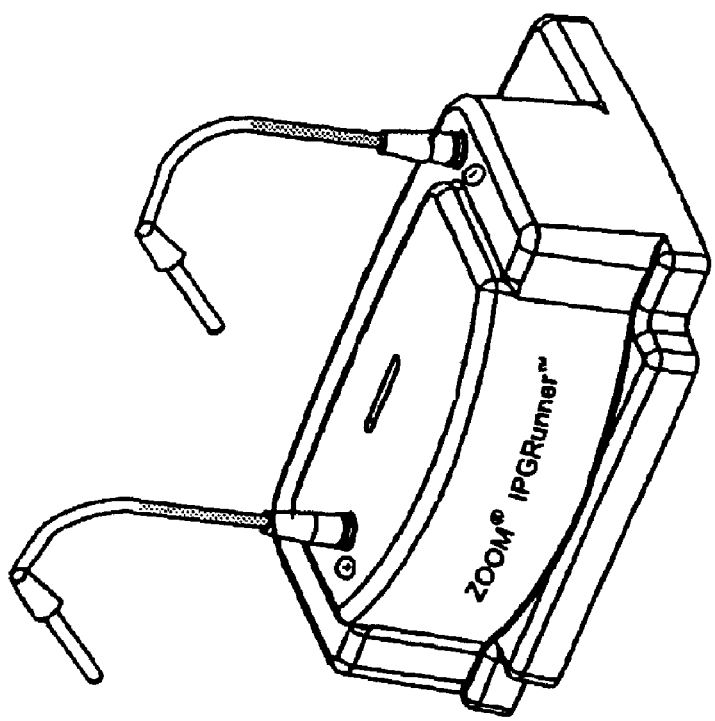
FIG. 11 illustrates an electrophoresis tank cover useful for applying voltage to the cassette and buffer core of the present invention.

Electrophoresis is conducted by attaching, via contact prongs 36 and 38, anode and cathode to a power supply. Conveniently, this may be performed by applying a cover having integrated electrodes, as illustrated in FIG. 11. The cover may usefully be designed so as to fit existing electrophoresis chambers, permitting their use with the present invention, but to interface only with buffer cores of the present invention.

A potential difference (voltage gradient) is applied that is sufficient to effect separation of analytes within the separation medium of strip 20. In embodiments in which strip 20 is an IPG strip, proteins, influenced by the voltage gradient, begin to migrate until the pI of the protein coincides with the pH on the immobilized gradient, at which point the focused protein ceases to move.

The voltage difference actually achieved by spaced electrical contact with strip 20 will always be less than that reported by the power supply, due to resistances inherent in the various connections between power supply and gel. In the cassette and buffer core of the present invention, such parasitic impedances include, e.g., (i) cable connections to the power supply, (ii) resistances in the cables themselves, (iii) cable-to-electrode contact resistance, (iv) electrode to wick contact resistance, (v) impedance of the wick itself, which is a function of the ionic concentration in the moist wick, which can vary during the run due to either endosmosis or diffusion, (vi) contact resistance between the wick and gel surface, which is influenced by the pressure of that interface, (vii) the inherent impedance of the gel.

In another aspect, the invention provides apparatus that provides a resistance pathway between power supply and prior-cast hydratable separation medium that is substantially lower than that found in prior art apparatus used for electrophoresis in the prior art; the reduced resistance substantially increases the efficiency with which prior-cast hydratable separation media, such as IPG strips, may be electrophoresed.

Of the parasitic impedances, the electrode-to-wick and wick-to-gel contact resistances can contribute significantly to the overall voltage drop from power supply to gel. These contact resistances depend upon the respective contact pressures. At any given compressive force applied inwardly against cassettes 100, the magnitude of these electrically effective contact pressures will depend upon the proportion of the force brought to bear at these locations. Accordingly, supports 28 and 30 may usefully be designed to distribute the external compressive force discontinuously, creating greater contact pressure at the first and second channel entries than elsewhere on cassette 100.

In a first series of exemplary embodiments, illustrated in FIGS. 6A-6C, the cassette contact faces of support 28 and support 30 are nonplanar: a plurality of discontinuous indentations collectively define a series of intervening protuberances. The serrated surface so created is capable of discontinuously distributing external compressive force to anode wire 31 and cathode wire 32.

In the embodiments shown, the indentations are sufficiently deep as to cause periodic discontinuities in the contact of the electrode wires to their respective supports. Such depth of indentation is not required.

Indentations are positioned so as to align each intervening protuberance with an entry 14 (equivalently for the other electrode, entry 16) of cassette 100. Indentations are sized so as to create protuberances with dimensions closely approximated to the lateral dimensions of entries 14 and 16.

For example, to minimize electrically ineffective contact (and thus maximize the proportion of electrically effective contact) with embodiments of cassette 100 that are capable of holding six strips 20, supports 28 and 30 have (on at least one cassette-contact face) six protuberances, each positioned to align with one of the six entries 14 (equivalently, entries 16) of cassette 100, and preferably sized to as to approximate the lateral dimensions of entries 14 and 16.

The faces of support 28 and support 30 that contact the same cassette 100 typically will have the same number of protuberances. However, for each of supports 28 and 30, the two cassette contact faces need not have the same number of protuberances (as is the case in the embodiments illustrated in FIGS. 6A-6C), if two cassettes 100 accommodating different numbers of strips 20 are to be applied to the two cassette contact faces. Typically, however, the two cassette contact faces will have the same number of protuberances.

In another series of embodiments (not shown), support 28 and support 30 lack indentations. Instead, the supports are nonunitary in construction, comprising materials that are differentially compressible. The least compressible materials are positioned to align with entries 14 (equivalently 16) of cassette 100; the more compressible materials are positioned to align elsewhere on cassette 100. The different degrees of compressibility cause differential distribution of the external compressive force, causing increased contact pressure at entries 14 (and 16).

The discontinuously applied pressures—occasioned, for example, by serrating the outward surfaces of supports 28 and 30, as in FIGS. 6A-6C—substantially improve the efficiency with which voltage (and current) can be applied to strips 20. Efficiency of voltage (and current) application to IPG strips, defined herein as the ratio, for a given voltage output from a power supply, of currents measured at identical strips 20 having identical samples, may be at least 2-fold better, 3-fold better, 4-fold better, even at least 5-fold better using the cassette and buffer core of the present invention as compared to horizontal, oil immersion IPG electrophoresis devices of the prior art. Efficiencies may even be at least 6-fold, 7-fold, 8-fold, 9-fold, and even at least 10-fold better. The data set forth in Examples 2 and 3 herein, plotted in FIGS. 9 and 10, demonstrate a 2-4 fold better efficiency than is observed using a prior art oil immersion flatbed IPG device.

The increased efficiency of electrical transmission provides significant advantages.

The increased efficiency permits IPG IEF to be performed using substantially lower power supply voltages and power supply currents, permitting less expensive power supplies, lacking current limitation means, to be used. The data set forth in Example 3 below demonstrates that even simple unregulated power supplies capable only of step voltage profiles may be used, obviating the need for power supplies capable of ramped voltage profiles.

The increased efficiency permits shorter run times to achieve the volt-hours required for focusing.

Using the cassette and buffer core of the present invention, focusing can be achieved in as few as 6 hours, 5 hours, 4 hours, even as few as 3.5 hours, 3.0 hours, 2.5 hours, 2.0 hours, or even as few as 1.5 or 1.25 hours, depending upon the sample, strip length, strip pH range, and voltage profile. Focusing can thus typically be achieved in 1.25-10 hours, 1.5-9 hours, 1.75-8 hours, 2-7 hours, 2.5-6 hours, and even in 1-3 hours.

Focusing can thus be achieved at least two times faster than with existing horizontal flatbed oil-immersion devices, often at least 3-times, 4-times, even 5-times faster. At times, focusing can be achieved at least 6-times, 7-times, 8-times, 9-times, even as much as 10-times faster.

For example, using a ramping power supply, a 7 cm IPG gel, a cassette capable of holding 6 such strips, and a buffer core with serrated supports, focusing can be achieved using the following ramped voltage profile:
  0-175 volts over 15 minutes
  175-2000 volts over 45 minutes
  2000 volts for 20-30 minutes.

Using a stepped power supply, a 7 cm IPG gel, a cassette capable of holding 6 such strips, and a buffer core with serrated supports, focusing can be achieved using the following stepped voltage profile:
  200 V for 20 minutes
  450 V for 15 minutes
  750 V for 15 minutes
  2000 V for 30 minutes.

Successful focusing can even be achieved using a constant power supply, such as the PowerEase® 500 (Invitrogen Corp., Carlsbad, Calif.), by applying
  500 V for 3-4 hours
  to a 7 cm IPG strip.

Accordingly, using the cassette and buffer core of the present invention, IPG isoelectric focusing can be achieved using maximal voltages as low as 3500 V, 3000 V, 2750 V, 2500 V, 2250 V, 2000 V, 1750 V, 1500 V, 1250V, 1000 V, and even as low as 750 V or 500 V, and may be achieved using a ramped voltage profile, stepped voltage profile, or a constant voltage profile. Minimal voltages may be 500 V, 750 V, 1000 V, 1250 V, 1500 V, 1750 V, 2000 V, 2250 V, even 2500 V or more.

Typically, electrical parameters required for effective isoelectric focusing using IPG strips are recited as a minimum, or desired, number of volt-hours, where volt-hours are defined as the cumulative sum of voltage times hours for each stage of a profile. As noted above, the volts nominally reported by the power supply are always greater than the voltages actually applied across the strip, the ratio of nominal to actual volt-hours depending upon the efficiency of the apparatus.

Prior art approaches to IEF using IPG strips typically call for at least 13,000 nominal volt-hours; some separations require as many as 36,000 nominal volt-hours.

The increased efficiency of the cassette and buffer core of the present invention permit focusing to be achieved in fewer than 13,000 nominal volt-hours, typically in fewer than 12,000 nominal volt-hours, 11,000 volt hours, 10,000 nominal volt hours, 9000 nominal volt hours, 8000 nominal volt hours, 7000 nominal volt-hours, 6000 nominal volt-hours, 5000 nominal volt-hours, 4000 nominal volt-hours, 3000 nominal volt-hours, even as few as 2000, 1900, 1800, 1700, 1600, 1500, 1400 or as few as 1300, 1200, 1100, or 1000 nominal volt-hours, for strips of 70 mm, 80 mm, 90 mm, 100 mm, 110 mm, 120 mm, 120 mm, 130 mm, 140 mm, 150 mm, 160 mm, 170 mm, 180 mm, 190 mm, 200 mm, 210 mm, 220 mm, 240 mm, or 240 mm, and for shorter, longer, or intermediate lengths.

Thus, focusing may be achieved after focusing for 1000-12,000 nominal volt-hours, 1100-11,000 nominal volt-hours, 1200-10,000 nominal volt-hours, 1300-9000 nominal volt-hours, 1400-8000 nominal volt-hours, and 1500-7000 nominal volt-hours, for strips of 70 mm, 80 mm, 90 mm, 100 mm, 110 mm, 120 mm, 120 mm, 130 mm, 140 mm, 150 mm, 160 mm, 170 mm, 180 mm, 190 mm, 200 mm, 210 mm, 220 mm, 240 mm, or 240 mm, and for shorter, longer, and intermediate length gels.

As is well known in the art, optimal voltage profiles and times will vary depending upon the sample, and may vary depending upon the power supply, the number of strips focused concurrently, and other variables known in the art, such as the pH range of the IPG strip. For example, pH 6-10 IPG strips may need to be focused for 30 minutes longer; similarly, crude protein mixtures or samples containing high salt concentration (e.g., >10 mM) may require longer run times or total volt hours for optimal resolution. It is well within the skill in the art to optimize focusing conditions empirically by routine experimentation, such as by varying any one or more of voltage, time, and profiles, starting with the above guidelines.

The increased electrical efficiency of the cassette and buffer core of the present invention, by permitting lower voltages and more efficient current application, reduces the propensity of IPG strips to undergo arcing and burning.

Upon completion of electrophoresis, buffer core 26 with cassettes 100 can be stored in a sealed container at −80° C. until strips are ready for analysis.

Strips 20 can, and typically will, be withdrawn from cavity 18 for further processing, with or without prior freezing. As described earlier, although strips 20 can at times be removed upon drying via channel entries 14 and 16, strips 20 will typically be removed by expanding the dimensions of cavity 18 of channel 12; in multilaminate embodiments of cassette 100, this is accomplished by separating laminate cover 42 from form-retaining member 10.

The buffer core embodiment above-described is designed to facilitate electrophoresis of a cassette in which, for each channel present therein, channel entries 14 and 16 permit electrical communication with the channel cavity 18 therebetween through a common surface of cassette 100, as is shown, e.g., in FIGS. 1-3.

Such a geometry is not required, however. The invention thus further provides a cassette in which entries 14 and 16 do not open through the same surface of form-retaining member 10, and a buffer core suited to electrophoresis of such a cassette. A principal advantage of such a geometry is that it can render the cassette compatible with buffer cores presently sold for slab gel SDS-polyacrylamide gel electrophoresis.

Figure 7A:
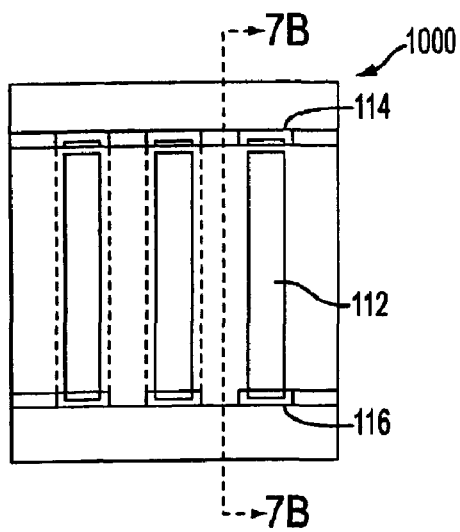
FIG. 7A is a front view of a cassette of the present invention in which channel entries open through opposite surfaces of the cassette.
Figure 7B:
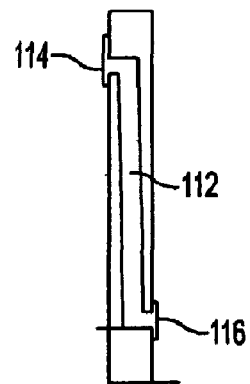
FIG. 7B is a side view of the cassette of FIG. 7A.

FIG. 7A is a front view, and FIG. 7B a side view, of a cassette 1000 of the present invention in which entries 114 and 116 of channels 112 respectively open through opposite surfaces of cassette 1000.

Channels 112 of cassette 1000, like channels 12 of cassette 100, are so dimensioned as to movingly engage a prior-cast hydratable electrophoretic separation medium in its dehydrated state and lodgingly enclose the strip after rehydration.

As should be apparent, in order to conduct electrophoresis using cassette 1000 as the enclosing member, cathode and anode must establish electrical communication with strip 20 from opposite sides of cassette 1000.

As when entries 14 and 16 open channel 12 to the same face of cassette 100, so too electrical communication of channel 112 through entries 114 and 116 can be direct, as by through-passage of electrodes through respective entries, or indirect, as by intermediation by polymer gels and/or conductive wicks. Additionally, however, when entries 114 and 116 open on opposite sides of cassette 1000, electrical communication can be established by contact of anode and cathode electrodes separately to a first and a second buffer reservoir, which reservoirs in turn separately contact entries 114 and 116.

In the latter case, first and second buffer reservoirs must be maintained in electrical isolation from one another, except by way of a circuit to be completed through the separation medium of strip 20.

Such geometry can readily be effected by sealingly contacting cassettes 1000, or a singular cassette 1000 and a buffer dam, to a buffer core 126, as further described in commonly-owned U.S. Pat. No. 5,888,369, incorporated herein by reference in its entirety, and as available commercially from Invitrogen Corp. (XCell II™ Buffer Core with Electrodes, catalogue no. EI9014X, Invitrogen Corp., Carlsbad, Calif.).

Figure 7C:
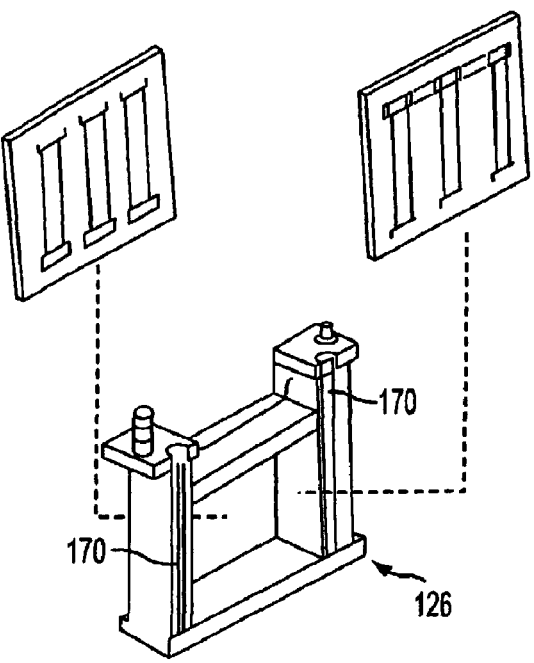
FIG. 7C is an exploded perspective view of two cassettes as shown in FIGS. 7A and 7B showing their operational relationship to a prior art buffer core.
Figure 7D:
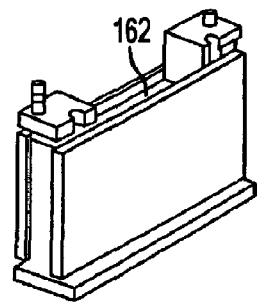
FIG. 7D is a perspective view of the cassettes of FIGS. 7A and 7B in operational contact with a prior art buffer core.

In order to conduct electrophoresis using such system, two cassettes 1000 (or a single cassette 1000 and a buffer dam) are lodgingly engaged in operational alignment with buffer core 126, as shown in FIGS. 7C and 7D.

The assembled buffer core and cassettes is then engaged in electrophoresis buffer chamber 34 which itself, or in conjunction with an additional device, urges cassettes 1000 (or singular cassette 1000 and buffer dam) into sealable contact with buffer core 126. Such additional device can usefully be a cam-activated clamp, such as that further described in U.S. Pat. No. 6,001,233, incorporated herein by reference in its entirety. Alternatively, buffer core 126 is first loosely engaged in electrophoresis buffer chamber 34, and cassettes thereafter aligned, contacted to, and then further urged against buffer core 126.

Fluid-tight contact between buffer core 126 and cassette 1000 (or a buffer dam) is typically, but optionally, further facilitated by a gasket, such as a silicone gasket, fitted into groove 170 of buffer core 126.

Buffer core 126 and cassettes 1000 (or singular cassette 1000 and buffer dam) in sealed engagement therewith define internal chamber 162 which, if cassettes 1000 are not overtopped, is fluidly noncommunicating with electrophoresis buffer chamber 34. A conductive solution is then added to internal chamber 162 to a level that (i) contacts cassette entries 114 (or 116, as the case may be) that open into chamber 162, and (ii) that does not overtop cassettes 1000. A conductive solution is also added to electrophoresis buffer chamber 34 to a level that (i) contacts the cassette entries 116 (or 114, as the case may be) that open into chamber 34, and (ii) that does not overtop cassettes 1000.

As further described in commonly-owned U.S. Pat. No. 5,888,369, and well known to users of the XCell™ SureLock system, the electrode geometry of buffer core 126 effects contact of the anode to internal chamber 126 and cathode to an external reservoir 60 formed in chamber 34, thus permitting the requisite voltage gradient to be applied across strip 20 to effect electrophoresis.

It should be noted that a potential disadvantage of direct contact of channels 112 and strips 20 with liquid reservoirs is the increased likelihood of ampholyte and/or sample leakage from the separation medium.

Although the cassettes of the present invention have been particularly described herein above as having at least one prior-formed channel with sufficient dimensional integrity as to permit the lodging by hydration of prior-cast hydratable separation media engaged there within, prior-formed channels are only one approach to hydratingly lodging such media within an enclosing member.

By way of example only, the enclosing member, if malleable yet shape-retaining, can be wrapped around the strip in its dehydrated form, fashioning a de novo channel which, upon hydration of the strip, lodgingly encloses the rehydrated strip there within.

In a further aspect, the present invention provides kits that facilitate the practice of the methods of the present invention.

The kits of the present invention may consist of at least one component (singularly or as a plurality thereof) selected from the group consisting of: a buffer core of the present invention, an electrophoresis chamber, an electrophoresis chamber lid that can establish electrical communication with a buffer core, a tension wedge, a buffer dam, an electrode wick, sealing tape, an IPG strip, containerized carrier ampholytes, containerized cathode buffer, containerized anode buffer, containerized stains (such as silver stains or colloidal blue stains), analyte standards, such as protein standards, typically in admixture, and a polyacrylamide gel suitable for performing a second dimension of separation.

Accordingly, a first series of kit embodiments may include nondisposable items useful for adapting electrophoresis devices to accommodate cassettes of the present invention. For example, a kit may include a buffer core of the present invention and corresponding lid.

For users who have neither electrophoresis chamber nor tension wedge, such as a cam-activated tension wedge, suitable to apply pressure that urges cassettes 100 inwardly against the buffer core, a kit of the present invention may include an electrophoresis chamber, tension wedge, buffer core and lid. Usefully, to permit a single cassette to be run, the kit may additionally optionally comprise a buffer dam.

A second series of kit embodiments may include disposable items suitable for use in the invention.

For example, a kit may include at least one cassette and a plurality of electrode wicks. The kit may optionally additionally comprise sealing tape suitable for sealing entries 14 and 16 during rehydration, and/or may optionally contain a plurality of IPG strips, either with identical pH ranges or differing pH ranges.

Kits of the present invention may also, optionally, include any one or more of separately containerized carrier ampholytes, cathode buffer, anode buffer, stains (such as silver stains or colloidal blue stains)—either in liquid form, at 1× use concentration or higher concentration for further dilution, or in dry form to be reconstituted with water of suitable quality—protein standards, typically in admixture, or polyacrylamide gels suitable for performing a second dimension of separation following isoelectric focusing, such as a Tris-Glycine ZOOM® gel (Invitrogen, Carlsbad, Calif.).

Example 1

Determination of Channel Tolerances

Three cassettes were manufactured by machining six parallel channels each into form-retaining plastic slabs, with geometry essentially as shown in FIG. 1A. The six channels of the first cassette all were 0.77 mm in depth, with two channels 4.09 mm in width, two channels 0.65 mm in width, and two channels 3.35 mm in width. The six channels of the second cassette all were 0.65 mm in depth, with two channels 4.09 mm in width, two channels 0.65 mm in width, and two channels 3.35 mm in width. The six channels of the third cassette all were 0.57 mm in depth, with two channels 4.09 mm in width, two channels 0.65 mm in width, and two channels 3.35 mm in width. The channels were rendered fluidly enclosing except at terminal entries by application of a flexible laminate cover to each of the three cassettes.

Serva IEF standard, 5 μL, (catalogue no. 39212-01, Serva Electrophoresis GmbH, Heidelberg, Germany) was mixed with 120 μL of rehydration buffer of the following composition: 8.0 M urea, 0.5% ampholytes (3-10 IPG buffer, cat. no. 17-6001-11, Amersham Biosciences), 2.0% (w/v) CHAPS, 20 mM DTT, 0.0025% (w/v) bromphenol blue. The solution was pipetted into each channel of the three cassettes, with the cassette positioned horizontally.

An Immobiline DryStrip 3-10 7 cm gel (Amersham Biosciences, Piscataway, N.J., USA) was inserted into each channel. The channel entries were occluded with cover tape and the strips allowed to rehydrate for 8 hours. Cover tape was removed, as were loading wells if present.

A filter paper wick dampened with water was placed in contact with the extreme ends of the gel portion of the strip at the terminal entries.

Electrodes were contacted to the wick at the anodic and cathodic ends of the cassette and a voltage applied in three steps according to the following protocol: 250 volts for 15 minutes, ramp from 250-3500 volts for 1 hour and 30 minutes, and 3500 volts for 1 hour. Current was limited to 1 mA and power to 4 watts in all three steps.

Strips were removed, stained with Coomassie blue stain, aligned, and photographed.

Figure 8:
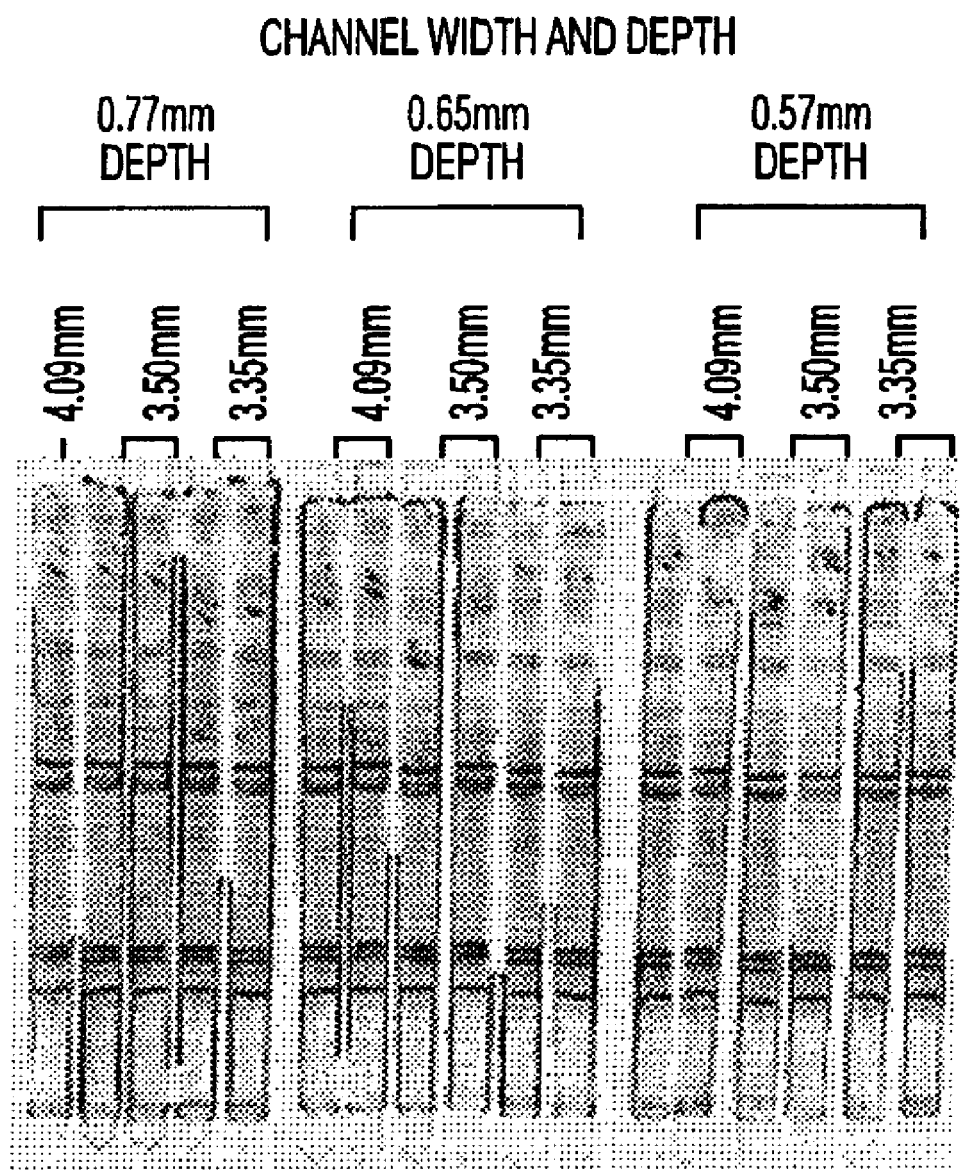
FIG. 8 shows IPG strips after electrophoresis in channels of the stated internal dimensions.

Results shown in FIG. 8 indicate that even the largest channel, 4.09 mm in width and 0.77 mm in depth, permitted adequate focusing of the Serva IEF standard (left-most lane) in strips with nominal width of 3 mm and depth of 0.5 mm.

Example 2

Comparison of Electrical Properties Using a Ramped Voltage Profile

This experiment compares the actual current flow through IPG strips run (i) in a commercial horizontal IPG electrophoresis apparatus (Multiphor™ flatbed system, Amersham Biosciences, Inc., Piscataway, N.J.) and (ii) in the cassette of the present invention using the buffer core of the present invention for vertical electrophoresis (ZOOM® IPGRunner™), using a ramped voltage power profile. For further comparison, strips from two vendors were used, Amersham Biosciences, Inc. ("AP strips") and Invitrogen Corporation ("INV strips").

Equipment and Materials

1. Power Supplies: Novex Model 35-40. A quantity of four of these units were used, one for each of the four individual experimental setups.
   a. Voltage/Time profile: The same ramped voltage profile was set for each of the four systems. The profile set was:
   0→250V over 15 minutes
   250V→3500 V over 1.5 hours
   3500V for 2 hours
2. Digital Multi Meters (DMMs) for measurement:
Two were used, both were capable of microampere measurements. The DMMs were used in current-measurement mode. They were set up in series with the ground side power cable between the apparatus and the power supply.
   a. Fluke 87 series III
   b. Fluke 73 series III
3. Multiphor™
   a. Wick solution: 0.5 ml ultra-pure water
   b. Rehydration: 0.125 ml/strip
4. ZOOM® IPGRunner™
   a. Wick solution: 0.75 ml de-ionized water
   b. Rehydration: 0.155 ml/strip
5. Strips
   a. Invitrogen 4-7 pH, Lot #100248
   b. AP Biotech 4-7 pH, Lot #287374
6. Sample in Rehydration Solution:
   a. second spin lysate from *E. Coli* (0.002 ml per 1 ml rehydration solution)
   b. after adding lysate, centrifuged 15 min at 14,000 rpm
   c. pH 4-7 ZOOMlytes (Invitrogen Corp.)

Results

TABLE 1

Actual Currents Using Multiphor ™ and ZOOM ® IPGRunner ™

| | CURRENT, mA, as measured (VOLTAGE, V, as reported by Power Supply) | | | |
|---|---|---|---|---|
| | Multiphor ™ | | ZOOM ® IPG Runner ™ | |
| | #1 w/AP strips | #2 w/Inv strips | #1 w/AP strips | #2 w/Inv strips |
| Elapsed Time (h:m) | | | | |
| 0:15 | .12 | .10 | .43 | .42 |
| 0:20 | .11 | .14 | .38 | .45 |
| ~0:25 | .145 | .185 | .33 | .53 |
| ~0:40 | .205 | Nr | .17 (1250 V) | .19 (1170 V) |
| ~0:50 | .088 (1710 V) | Nr | nr | .20 (1515 V) |
| ~1:00 | .097 (2100 V) | .100 (1908 V) | .24 (2108 V) | .24 (1908 V) |
| ~1:15 | Nr | .097 (2500 V) | nr | .29 (2500 V) |
| Time @ 3500 V: | | | | |
| 0:05 | .15 (3500 V) | .12 (3500 V) | .39 (3500 V) | .39 (3500 V) |
| 0:10 | .15 (3500 V) | .12 (3500 V) | .45 [1] | .38 (3500 V) |
| 0:15 | .15 (3500 V) | .12 (3500 V) | .46 (3500 V) | .35 (3500 V) |
| 0:20 | .15 (3500 V) | .11 (3500 V) | .42 (3500 V) | .32 (3500 V) |
| 0:30 | .15 (3500 V) | .11 (3500 V) | .36 (3500 V) | .30 (3500 V) |
| 1:15 | .15 (3500 V) | .11 (3500 V) | .27 (3500 V) | .65/.28 [2] |
| 1:40 | | | .20 (3500 V) | .20 (3500 V) | nr = not recorded

Notes for Table 1

[1] One strip burned on the acidic end after 10 minutes at 3500 V. The burn was active for 5 minutes, after which the current dropped back down.
[2] Burning/After-burned currents. One strip began burning after 1 hour and 15 minutes at 3500 V. The burn was active for 7 minutes. The Power Limit of the power supply was met, and so the voltage dropped when the current spiked during the burn. For instance, at .65 mA the voltage was 2900. The highest recorded current (100 ms sampling) was .82 mA during the burn.
[3] Currents were measured only for 1 hour, 40 minutes of the 2 hour 3500 V step.

Figure 9:
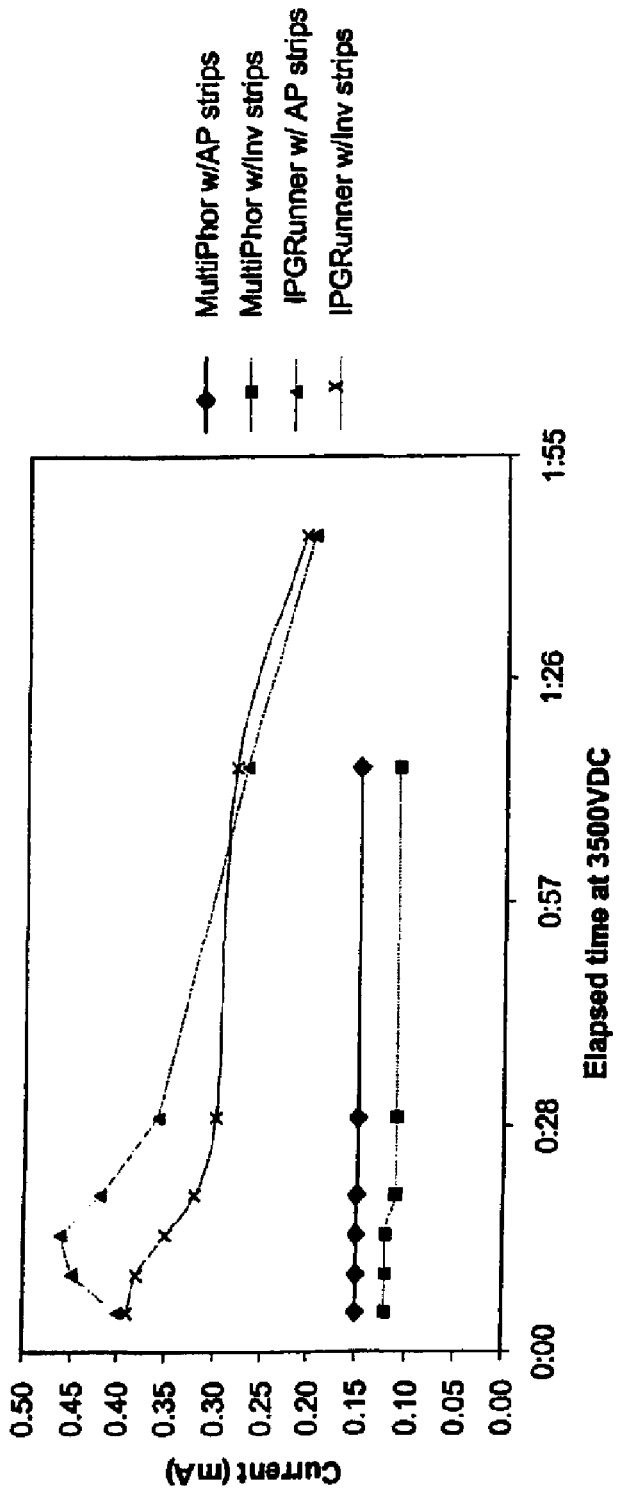
FIG. 9 plots measured currents through IPG strips run, for comparison, in the cassette of the present invention using the buffer core of the present invention, and in a commercially available horizontal flat bed apparatus, using identical power supplies with identical voltage programs.

Results are plotted in FIG. 9. As can be seen from both Table 1 and FIG. 9, there is substantially higher current flow through the IPG strips using the cassette and buffer core of the present invention as compared to a flatbed device, at all times during the run and with either brand of IPG strip.

Table 2 presents "volt-hour" ratios for the two types of devices during the constant 3500 Volt period of the power cycle program.

The "volt-hour" ratios are calculated from the measured currents—given identity in resistance through the IPG strips, measured current-hour ratios are equivalent to volt-hour ratios. Ratios are calculated as IPGRunner™ (IPGRunner) "volt-hours" divided Multiphor™ (MP) "volt-hours".

TABLE 2

"Volt-hour" Ratios

V-hour ratios @3500 V: IPGRunner/MP

| Time | AP strips | INV strips |
|---|---|---|
| 0:05:00 | 2.7 | 3.3 |
| 0:10:00 | 3.0 | 3.2 |
| 0:15:00 | 3.1 | 2.9 |
| 0:20:00 | 2.8 | 2.9 |
| 0:30:00 | 2.4 | 2.7 |
| 1:15:00 | 1.8 | 2.5 |
| Average | 2.6 | 2.9 |

Table 2 demonstrates that the cassette and buffer core of the present invention are far more efficient at transferring power to the gels than is the flatbed Multiphor™, despite apparent identity in the nominal volt-hours calculated by multiplying power supply voltage by time.

During the first, low voltage, stage of the profile, the cassette and buffer core of the present invention pushes up to 4 times the amount of current through the strips (both AP and INV strips) than the Multiphor™ does. There were visible differences in the velocity and shape of the dye fronts between the two apparatuses during this stage.

During the high voltage focusing plateau, set at 3500 V in this experiment, the cassette and buffer core of the present invention delivered an average of approximately 2.6 times and 2.9 times more current to the AP and INV strips, respectively, than did the Multiphor™.

Using a ramped voltage profile, lower voltages and times may be used to achieve focusing with the cassette and buffer core of the present invention than has been used for prior flat bed devices. Lower voltages for shorter periods are more convenient, require less sophisticated (and expensive) power supplies, obviate the need for current limiting power supplies, and should lead to less frequent arcing and thus burning of the strips. Optimal voltages and times will, as before, depend in part on sample osmolality and electrolyte concentration.

Example 3

Electrical Properties Using a Stepped Voltage Profile

Four full cassettes with six strips each of various pH ranges, each strip loaded with a standard sample, were run in two ZOOM® IPGRunner™ systems (cassette, buffer core, tank) of the present invention in order to evaluate the effectiveness of a voltage step profile without current or watt limits.

Equipment and Materials
1. Power Supplies: Novex Model 35-40. A quantity of two of these units were used, one for each of the two individual experimental setups.
   a. Voltage/Time profile: The same voltage profile was set on both systems, as set forth in Table 3, below.
2. Digital Multi Meters for measurement. Two were used, both capable of micro Amp measurements. The DMMs were used in current-measurement mode. They were set up in series with the ground-side power cable between the apparatus and the power supply.
   a. Fluke 87 series III
   b. Fluke 73 series III

TABLE 3

Stepped Voltage Profile

| Voltage | Duration | Time, accumulated |
|---|---|---|
| 175 | 15 min | 0:00-0:15 |
| 500 | 15 min | 0:15-0:30 |
| 750 | 15 min | 0:30-0:45 |
| 2000 | 30 min | 0:45-1:15 |

Results

Figure 10:
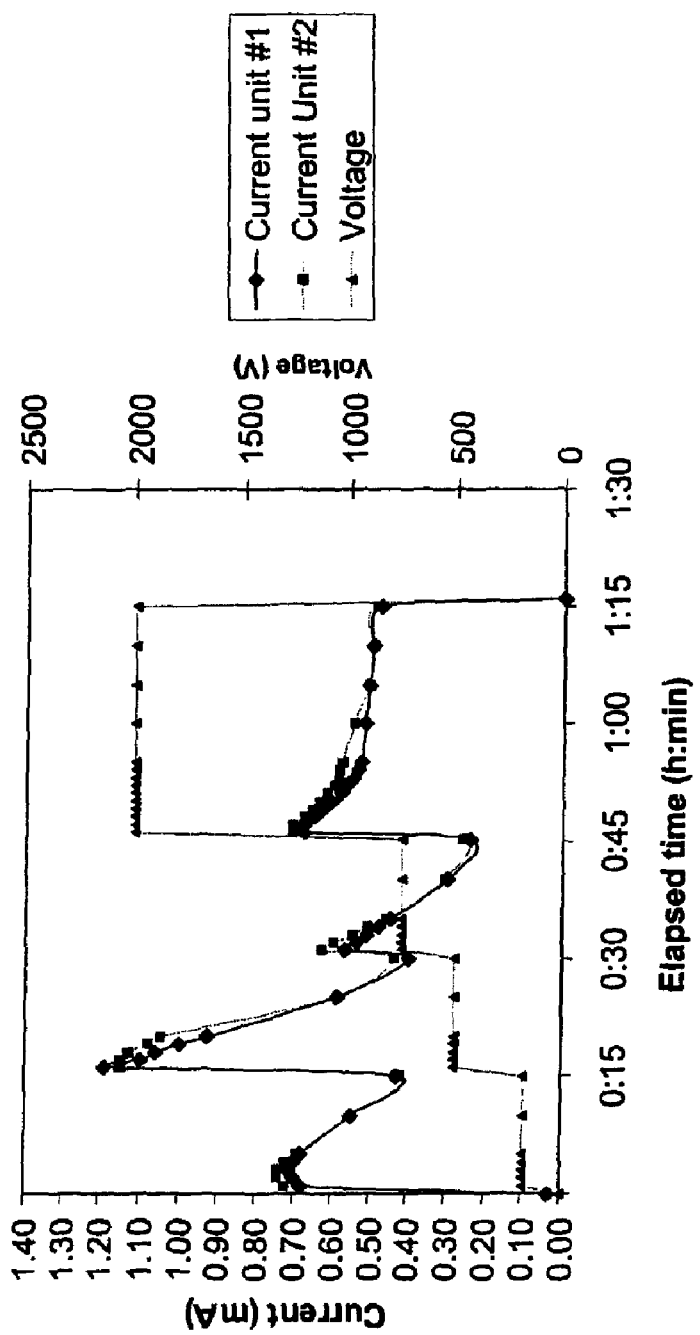
FIG. 10 plots currents measured through IPG strips, and voltages reported by two power supplies, using the cassette and buffer core of the present invention, with focusing performed using a stepped voltage profile.

Results are summarized in Table 4 and plotted in FIG. 10.

TABLE 4

Measured Current and Nominal Voltages, Step Profile

CURRENT, mA, as measured (VOLTAGE, V, as reported by Power Supply)

| Elapsed Time (h:m) | ZOOM® IPG Runner™ (power unit #1) | | ZOOM® IPG Runner™ (power unit #2) | |
|---|---|---|---|---|
| | Current | Voltage | Current | Voltage |
| 0:00 | .03 | 0 | 0.03 | 0 |
| 0:01 | .68 | 175 | .72 | 175 |
| 0:02 | .70 | 175 | .74 | 175 |
| 0:03 | .71 | 175 | .74 | 175 |
| 0:04 | .70 | 175 | .72 | 175 |
| 0:05 | .68 | 175 | .69 | 175 |
| 0:10 | .55 | 175 | .55 | 175 |
| 0:15 | .43/1.21 | 175/500 | .42/1.20 | 175/500 |
| 0:16 | 1.19 | 500 | 1.15 | 500 |
| 0:17 | 1.10 | 500 | 1.15 | 500 |
| 0:18 | 1.06 | 500 | 1.13 | 500 |
| 0:19 | 1.00 | 500 | 1.08 | 500 |
| 0:20 | .93 | 500 | 1.05 | 500 |
| 0:25 | .59 | 500 | .59 | 500 |
| 0:30 | .40/.60 | 500/750 | .44/.66 | 500/750 |
| 0:31 | .57 | 750 | .63 | 750 |
| 0:32 | .54 | 750 | .60 | 750 |
| 0:33 | .51 | 750 | .55 | 750 |
| 0:34 | .48 | 750 | .51 | 750 |
| 0:35 | .45 | 750 | .46 | 750 |
| 0:40 | .30 | 750 | .31 | 750 |
| 0:45 | .24/.67 | 750/2000 | .26/.72 | 750/2000 |
| 0:46 | .68 | 2000 | .71 | 2000 |
| 0:47 | .68 | 2000 | .71 | 2000 |
| 0:48 | .65 | 2000 | .68 | 2000 |
| 0:49 | .63 | 2000 | .66 | 2000 |
| 0:50 | .61 | 2000 | .64 | 2000 |
| 0:51 | .58 | 2000 | .62 | 2000 |
| 0:52 | .57 | 2000 | .60 | 2000 |
| 0:53 | .55 | 2000 | .59 | 2000 |
| 0:54 | .54 | 2000 | .59 | 2000 |
| 0:55 | .53 | 2000 | ..58 | 2000 |
| 1:00 | .52 | 2000 | .55 | 2000 |
| 1:05 | .51 | 2000 | .51 | 2000 |
| 1:10 | .50 | 2000 | .50 | 2000 |
| 1:15 | .48/0.01 | 2000/0.0 | .49 | 2000 |
| 1:45 | finished | finished | | 2000/0 |

Notes for Table 4:
[1] No strips burned.

The stepped voltage profile resulted in no burning of any of the 24 strips.

The 500 volt step resulted in 99 µamps per strip for less than a minute, but was over 70 µamps for approximately 5 minutes; however, 500 volts is a significantly lower voltage than the final focusing voltage, and the conductivity of the sample at this low voltage is not likely to cause any arcing or burning. No arcing or burning was seen.

This experiment demonstrates that an inexpensive unregulated power supply capable of only "step" profiles can be used to focus samples using a variety of IPG strips with the cassette and buffer core (ZOOM® IPGRunner™ system) of the present invention, without burning of the strips, and with high quality isoelectric focusing. The power supplies are programmable but do not provide current limits in the microampere range.

Additionally, the tested profile appears to provide an excellent balance by placing the higher current loads down in the lower voltage regions. Optimal voltages and times will, however, depend in part on sample osmolality and electrolyte concentration.

All patents and publications cited in this specification are herein incorporated by reference as if each had specifically and individually been incorporated by reference herein. Although the foregoing invention has been described in some detail by way of illustration and example, it will be readily apparent to those of ordinary skill in the art, in light of the teachings herein, that certain changes and modifications may be made thereto without departing from the spirit or scope of the appended claims, which, along with their full range of equivalents, alone define the scope of invention.

What is claimed is:

1. A system for low resistance electrophoresis of analyte samples in prior-cast, hydratable separation media strips, comprising:
   means for enclosing a plurality of said strips, said enclosing means permitting spaced electrical communication separately with each of said enclosed strips through respective first and second entries; and
   means responsive to an external compressive force for effecting spaced electrical communication by a single anode and single cathode simultaneously with each of said enclosed strips,
   wherein said electrical communication means is capable of distributing an external compressive force to urge said anode and said cathode toward said enclosing means with greater pressure at said first and second entries than elsewhere on said enclosing means.

2. The system of claim 1, wherein said enclosing means is capable of hydratingly lodging said strips there within.

3. The system of claim 2, wherein said electrical communication means comprises:
   an anode support;
   a cathode support;
   an anode; and
   a cathode;
   wherein said supports discontinuously distribute an external compressive force to said anode and cathode to urge said anode and said cathode toward said enclosing means with greater pressure at said first and second entries than elsewhere on said enclosing means.

4. The system of claim 2, wherein said anode support makes discontinuous contact with said anode and said cathode support makes discontinuous contact with said cathode.

5. The system of claim 1, capable of electrophoretic separation in said strips with application of 3000 or fewer volts.

6. The system of claim 5, capable of electrophoretic separation in said strips with application of 1500 or fewer volts.

7. The system of claim 6, capable of electrophoretic separation in said strips with application of 500 or fewer volts.

8. The system of claim 1, capable of electrophoretic separation in said strips with application of fewer than 2000 volt-hours.

9. The system of claim 8, capable of electrophoretic separation in said strips with application of fewer than 1500 volt-hours.

10. The system of claim 1, capable of electrophoretic separation in said strips in fewer than 6 hours.

11. The system of claim 10, capable of electrophoretic separation in said strips in fewer than 5 hours.

12. The system of claim 10, capable of electrophoretic separation in said strips in fewer than 4 hours.

13. A method for low resistance electrophoresis of analyte samples in prior-cast, hydratable separation media strips, the method comprising:
   hydratingly lodging at least one strip within an enclosing member that permits separate, spaced, electrical communication with each of a plurality of enclosed strips through respective first and second entries;
   applying a sample containing protein analytes to said at least one strip;
   forcibly urging an anode and a cathode toward said enclosing member to effect simultaneous spaced electrical communication with each of said strips, wherein the force urging said anode and said cathode toward said enclosing member is distributed to create greater contact pressure at said first and second entries than elsewhere on said enclosing member; and then
   applying electrical potentials to said anode and said cathode at a potential difference and for a time sufficient to effect electrophoretic separation of analytes in said at least one strip.

14. The method of claim 13, wherein said sample is applied during lodging of said strip in said enclosing member.

15. The method of claim 13, wherein said applied potential difference is 3000 or fewer volts.

16. The method of claim 15, wherein said applied potential difference is 1500 or fewer volts.

17. The method of claim 16, wherein said applied potential difference is 500 or fewer volts.

18. The method of claim 13, wherein said potential difference is applied for fewer than 6 hours.

19. The method of claim 18, wherein said potential difference is applied for fewer than 5 hours.

20. The method of claim 19, wherein said potential difference is applied for fewer than 4 hours.

* * * * *